United States Patent [19]

Mitchell-Olds et al.

[11] Patent Number: 5,770,789
[45] Date of Patent: Jun. 23, 1998

[54] HERITABLE REDUCTION IN INSECT FEEDING ON BRASSICACEAE PLANTS

[75] Inventors: Storrs Thomas Mitchell-Olds; David Henry Siemens, both of Missoula, Mont.

[73] Assignee: University of Montana, Missoula, Mont.

[21] Appl. No.: 496,016

[22] Filed: Jun. 28, 1995

[51] Int. Cl.⁶ .............................. A01H 5/00; A01H 1/04; A01H 1/06; C12N 15/01

[52] U.S. Cl. .................. 800/200; 800/230; 800/DIG. 15; 800/DIG. 17; 435/6; 435/172.1; 47/58; 47/DIG. 1

[58] Field of Search ........................ 435/172.1, 6; 47/58, 47/DIG. 1; 800/200, 230, DIG. 17, DIG. 15

[56] References Cited

PUBLICATIONS

Berenbaum et al., *Plant Resistance to Herbivores and Pathogens Ecology, Evolution, and Genetics*, Chapter 4:69–87 (1987), Univ. Chicago Press, Chicago.
James et al., *Physiologia Plantarium*, 82:163–170, (1991).
Koritsas et al., *Ann. Appl. Biol.*, 118:209–221, (1991).
Lister et al., *Plant J.*, 4:745–750, (1993) No. 4.
Magrath et al., *Heredity*, 72:290–299, (1994) No. 3 Mar.
Magrath et al., *Plant Breeding*, 111:55–72, (1993).
Richard Mithen, *Euphytica*, 63:71–83, (1992).
Mithen et al., *Plant Breeding*, 108:60–68, (1992) No. 1.
Parkin et al., *Heredity*, 72:594–598, (1994).
Thangstad et al., *Plant Molecular Biol.*, 23:511–524, (1993).
Giamoustaris et al., Ann. appl. Biol. 126:347–363, 1995.
F.S. Chew, "Searching for Defensive Chemistry in the Cruciferae, or, do Glucosinolates Always Control with Their Potential Herbivores and Symbionts? No!," *Chemical Mediation and Coevolution*, Ed., Kevin C. Spencer, Academic Press, Inc., Ch. 4, pp. 81–112 (1988).

Lenman et al., "Differential Expression of Myrosinase Gene Families," *Plant Physiol.*, 103:703–7111 (1993).
Xue et al., "The glucosinolate–degrading enzyme myrosinase in Brassicaceae is encoded by a gene family," *Plant Molecular Biology*, 18: 387–398 (1992).
Höglund et al., "Distribution of Myrosinase in Rapeseed Tissues," *Plant Physiol.*, 95: 213–221 (1991).
Ibrahim et al., "Engineering Altered Glucosinolate Biosynthesis by Two Alternative Strategies," *Genetic Enginering of Plant Secondary Metabolism*, Ed., Ellis et al., Plenum Press, New York, pp. 125–152 (1994).
Hicks, "Mustard Oil Glucosides: Feeding Stimulants for Adult Cabbage Flea Bettles, *Phyllotreta cruciferae* (Coleoptera: Chrysomelidae)," *Ann. Ent. Soc. Am*, 67: 261–264 (1974).
Reed et al. 1989 Entomol. exp. appl. 53(3):277–286.
Bartlet et al. 1994. Entomol. exp. appl. 73(1):77–83.
Butts et al. 1990. J. Econ. Entomol. 83(6):2258–2262.
Bodnaryk et al. 1990. J. Chem. Ecol. 16(9):2735–46.
Haughn et al. 1991. Plant Physiol. 97(1):217–226.
Mithen et al. 1987. Phytochemistry 26(7): 1969–1973.
Jarvis et al. 1994. Plant Mol. Biol. 24(4):685–687.

*Primary Examiner*—David T. Fox
*Attorney, Agent, or Firm*—Fish & Richardson, P.C.

[57] ABSTRACT

A method for producing plants of the Brassicaceae family that have reduced feeding by cruciferous insects is disclosed. The method comprises selecting for the heritable trait of altered total non-seed glucosinolate levels or for the heritable trait of increased myrosinase activity. Selection may be performed on Brassicaceae cultivars, mutagenized populations or wild populations, including the species *Brassica napus, B. campestris* and *Arabidopsis thaliana*. Plants having such altered levels show reduced feeding by cruciferous insects, including flea beetle, diamond back moth and cabbage butterfly. Plants selected for altered levels of both glucosinolates and myrosinase also show reduced feeding by cruciferous insects.

25 Claims, 5 Drawing Sheets

HERITABLE REDUCTION IN INSECT FEEDING ON BRASSICACEAE PLANTS

STATEMENT AS TO FEDERALLY SPONSORED RESEARCH

Some of the research disclosed herein was supported by United States Department of Agriculture Grant Nos. 92-37303-7613 and 93-37302-9572, and National Science Foundation Grant No. BSR-9021451. The United States government may have certain rights in this invention.

FIELD OF THE INVENTION

This invention relates to plants having a heritable reduction in feeding by insects upon cotyledons or leaves. More particularly, the invention relates to plants of the family Brassicaceae that have a heritable alteration in total non-seed glucosinolate levels and/or alteration in myrosinase levels that results in a reduction in susceptibility to feeding damage by cruciferous insects.

BACKGROUND OF THE INVENTION

Plants of the family Brassicaceae comprise species important in agriculture and research. Plants within this family include *Brassica rapa* (campestris), *B. napus, B. oleraceae* and *Arabidopsis thaliana*. Certain members of the genus Brassica are also known as oilseed rape or canola and are useful in the production of industrial and edible oils, including canola oil. *Arabidopsis thaliana* is often used for research purposes.

Efficient and cost-effective production from such plants is subject to numerous problems, including damage due to feeding by various insects. Insects that can cause serious damage to Brassicaceae include flea beetles (e.g., *Phyllotreta crucifereae* and *P. striolata* (F.)). These insects are members of the order Coleoptera and cause damage to leaves and cotyledons of Brassicaceae plants in both the larvae and adult stages. Other insects which can cause serious damage to Brassicaceae plants include members of the order Lepidoptera, such as diamond back moth (*Plutella xylostella*) and cabbage butterfly (*Pieris rapea*).

Glucosinolates are a family of sulfur-containing compounds found in many plant species, including members of the Brassicaceae. Larsen, P., in *The Biochemistry of Plants*, Conn, E., ed., Vol. 7, Academic Press, New York, 1981, pp. 501–525; Chew, F., in *Chemical Mediation of Coevolution*, Academic Press, New York, 1988, pp. 81–112. Glucosinolates contain a glycoside moiety and a variable side chain, including aliphatic alkenyl groups, indolyl groups or aralkyl groups.

Glucosinolates can be hydrolyzed by myrosinase (thioglucoside glucohydrolase, E.C. 3.2.3.1) at the S-glucose bond to produce D-glucose and an unstable aglycone. The aglycone rearranges to form sulfate and products that depend on the particular side chain of the compound being hydrolyzed. Breakdown products include isothiocyanates (volatile mustard oils), thiocyanates and nitriles (Larsen, supra). Myrosinase isozymes appear to differ in pH optima but do not appear to differ in their specificity for particular glucosinolate compounds.

Glucosinolates and myrosinase can occur in all parts of the plant, but are separated cellularly or subcellularly in intact plant tissue. When plant tissue is damaged, e.g., by crushing or by insect feeding, myrosinase and glucosinolates are brought into contact and production of the hydrolysis products ensues (Chew, F., supra).

Glucosinolate levels in the plant can vary with environmental factors such as nutrients (e.g., available soil nitrogen), water, and light intensity. Louda, S. and Rodman, J., J. Chem. Ecol. 9:397–422 (1983); Wolfson, J., Environ. Entomol. 11:207–213 (1982); Gershenzon, J., Recent Adv. Phytochem. 18:273–320 (1984).

Glucosinolates and glucosinolate degradation products render the meal produced from rape or canola seeds unpalatable or toxic to animals to whom the meal is fed. During the last two decades, rape varieties have been bred that have a seed-specific reduction in glucosinolate levels. It is also known that, in seeds, low glucosinolate levels are recessive to high glucosinolate levels.

Studies have been performed to ascertain the effect of glucosinolates on insect behavior. Glucosinolate-related compounds have been painted on plants, and glucosinolates and glucosinolate-related compounds have been added to artificial diets, followed by observations of any effects on insect behavior. The results indicate that such compounds can affect feeding behavior and oviposition responses (Chew 1988). In general, glucosinolates and their breakdown products may act as oviposition deterrents and feeding toxins to non-adapted herbivores, and as attractants and feeding stimulants to species of insect herbivores that specialize on mustards. Examples of mustard specialists include flea beetles, cabbage butterfly and diamondback moth. Of particular importance is the herbivore *P. cruciferae* which mainly attacks seedlings and which is known to have a significant negative impact on total seed set, seed weight, and seedling survivorship of rape plants. (Pilson, D., Bull. Ecol. Soc. Am. 74:394 (1993).

SUMMARY OF THE INVENTION

Methods are disclosed for producing a plant having a heritable reduction in susceptibility to cotyledon or leaf feeding by cruciferous insects. The method comprises: selecting, in a population of $P_0$ Brassicaceae plants, at least one $P_0$ plant having a total non-seed glucosinolate level that is decreased sufficiently, relative to the total non-seed glucosinolate level in the $P_0$ population, to reduce susceptibility to cotyledon or leaf feeding by cruciferous insects; producing progeny (termed $P_1$ plants) from the $P_0$ plant; and identifying at least one $P_1$ plant that inherits the decreased total non-seed glucosinolate level, thereby producing a plant having reduced susceptibility to cotyledon or leaf feeding by insects. The $P_0$ plant may be selected from plants in the 0–15 percentile for total non-seed glucosinolates in the $P_0$ population.

In another embodiment, at least one $P_0$ plant is selected from a population of $P_0$ Brassicaceae plants having a mean total non-seed glucosinolate level. The $P_0$ plant has a total non-seed glucosinolate level that is increased sufficiently, relative to the total non-seed glucosinolate level in the $P_0$ population, to reduce susceptibility to cotyledon or leaf feeding by cruciferous insects. $P_1$ progeny are produced for the at least one $P_0$ plant and at least one $P_1$ plant is identified that inherits the increased total non-seed glucosinolate levels, thereby producing a plant having reduced susceptibility to cotyledon or leaf feeding by insects. The $P_0$ plant may be selected from plants in the 85–100 percentile for total non-seed glucosinolates in the $P_0$ population.

In another embodiment, at least one $P_0$ plant is selected from a population of $P_0$ Brassicaceae plants having a mean myrosinase activity. The $P_0$ plant has a level of myrosinase activity that is increased sufficiently, relative to the myrosinase activity in the $P_0$ population, to reduce susceptibility to cotyledon or leaf feeding by cruciferous insects. $P_1$ progeny are produced from the $P_0$ plant and at least one $P_1$ plant is identified that inherits the increased myrosinase activity, thereby producing a plant having reduced susceptibility to cotyledon or leaf feeding by insects. The $P_0$ plant may be selected from plants in the 85–100 percentile for myrosinase activity in the $P_0$ population.

At least one $P_0$ plant selected for increased myrosinase activity may be further selected to have a level of total non-seed glucosinolates that is increased sufficiently, relative to a mean total non-seed glucosinolate level in the $P_0$ population, to reduce susceptibility to cotyledon or leaf feeding by cruciferous insects.

$P_1$ progeny may be produced by selfing. $P_1$ progeny may also be produced, when a plurality of $P_0$ plants having altered total non-seed glucosinolate level and/or increased myrosinase activity are selected, by making crosses among the plurality of $P_0$ plants.

The $P_0$ population may comprise plants grown from mutagenized seeds. In some embodiments, a $P_0$ population may comprise plants genetically engineered for altered total non-seed glucosinolate levels. In some embodiments, a $P_0$ population may comprise plants genetically engineered for increased myrosinase activity, e.g., plants having a recombinant DNA construct expressing a myrosinase coding sequence.

A $P_0$ plant or a $P_1$ plant may be identified by genetic linkage between altered total non-seed glucosinolate level and a polymorphic genetic marker, e.g., a nucleic acid having substantial sequence similarity to at least 50 nucleotides from Arabidopsis RFLP probe g6842 or pCITd23. In some embodiments, a $P_0$ or $P_1$ plant may be identified by genetic linkage between increased myrosinase activity and a polymorphic genetic marker, e.g., a nucleic acid having substantial sequence similarity to at least 50 nucleotides from Arabidopsis RFLP probe m106.

A $P_1$ plant preferably is a *Brassica campestris* plant or a *Brassica napus* plant.

DESCRIPTION OF THE PREFERRED EMBODIMENTS

Figure 1:
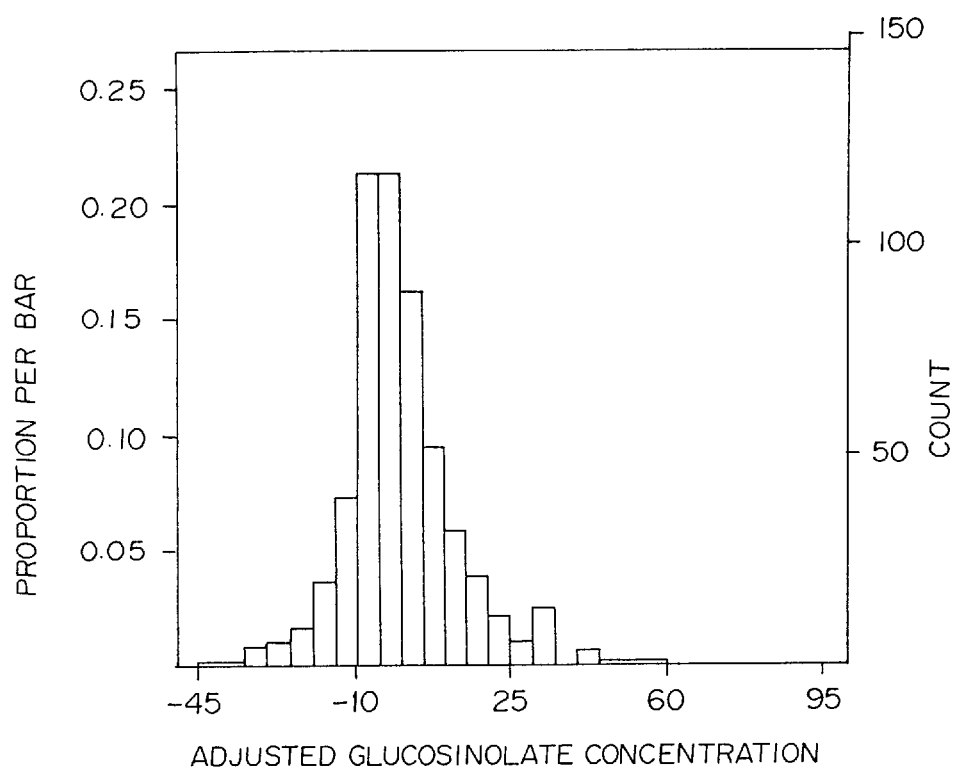
FIG. 1 is a histogram showing the frequency distribution of the developmentally adjusted total non-seed glucosinolate levels in a $P_0$ population of Brassica rapa.

Heretofore, it has not been possible to predict whether heritable alterations in glucosinolate levels can be selected in Brassicaceae plant populations or, if such alterations could have been selected, whether insect feeding on whole plants would be affected. The inventors have discovered that a plant of the family Brassicaceae can be bred to have a heritable alteration in the level of total non-seed glucosinolates or the level of myrosinase activity. Surprisingly, plants having such heritable traits can be selected and show a reduction in susceptibility to cotyledon and leaf feeding by insect pests, including flea beetles and diamondback moths.

A plant according to the invention is produced from a population of Brassicaceae plants from a single species, herein termed a $P_0$ population. This population may be, for example, a single uniform population of wild plants, an $F_1$ population derived from two cultivars, or a population of plants from a single cultivar. The size of the $P_0$ population to be used depends upon the genetic variation present in the population and on the intensity of the selection pressure that is to be applied. See, e.g., Downey, R. and Rakow, G. in *Principles of Cultivar Development*, Vol. 2: Crop Species, Fehr, W., Ed., McMillan Publishing, New York, (1987), pages 437–486. Generally, a smaller $P_0$ population can be used if a large amount of genetic variation is known or expected to be present in the population. A smaller $P_0$ population size, e.g., from about 100 to about 1000 plants, also can be used if it is desired to apply less intense selection pressure. On the other hand, a larger population size, e.g., from about 500 to about 30,000 plants, can be used if less genetic variation is present or if more intense selection pressure is to be applied.

A $P_0$ population may comprise plants grown from mutagenized seeds, which have greater genetic variation than corresponding non-mutagenized seeds. Mutagenesis typically increases the genetic variation for total non-seed glucosinolate levels. Chemical mutagens, including but not limited to, ethidium bromide, nitrosoguanidine, diepoxybutane, ethylnitrosourea and ethyl methane sulfonate may be used to create a $P_0$ population. Alternatively, physical mutagens such as X-rays, UV rays may be used. Mutagenesis treatment may also be applied to other plant tissues, such as cell cultures, embryos, microspores and shoot apices. Plants formed from such mutagenized tissues may be used in a $P_0$ population.

A $P_0$ population may comprise plants that have been genetically engineered for decreased total non-seed glucosinolate levels. Such genetic engineering may comprise, for example, sense or anti-sense constructs designed to alter expression of glucosinolate biosynthesis genes. Alternatively, such genetically engineered plants may comprise insertional mutants that eliminate expression of a biosynthesis gene.

Individual plants, e.g., seedlings, in the population are assayed for the level of total non-seed glucosinolates. Tissues to be analyzed for total non-seed glucosinolate levels may be any non-seed tissue, e.g., stems, cotyledons, leaves and the like. Preferred tissues are cotyledons or first true leaves of seedlings about 6 to about 50 days of age. The assay is preferably carried out before onset of flowering, so that only those plants having the desired level of glucosinolates need to pollinated and advanced to the next generation.

Glucosinolate assay methods are known in art. See, e.g., Heaney, R. and Fenwick, G., Z. Pflazenzuchtg. 87:89–95 (1981). Assays may measure glucosinolates by, e.g., high performance liquid chromatography (HPLC) analysis of non-seed extracts or the amount of glucose released after enzymatic hydrolysis of glucosinolates in non-seed extracts. If desired, an assay may be adapted to the use of microtiter plates for rapid analysis of large numbers of samples. The absolute level of total non-seed glucosinolates need not be measured. Rather, measuring the level relative to the average of the population is sufficient to perform the method of the invention.

From the glucosinolate analysis a frequency distribution of total non-seed glucosinolate levels may be plotted and individual plants selected for advancement to the next generation. A plant produced according to the invention may be selected to have either a higher or a lower level of total non-seed glucosinolates than the starting $P_0$ population from which such a plant is derived. Those plants having a total glucosinolate level about ½ standard deviation above or below the mean glucosinolate level of the $P_0$ population are likely candidates to have a heritable alteration in total glucosinolate level. Such plants will typically be in either the 0–15 percentile or the 85–100 percentile for total non-seed glucosinolate level.

If desired, $P_0$ plants may be evaluated on the basis of a Z-distribution. Zar, J., *Biostatistical Analysis*, 2nd Ed., Prentice-Hall, Englewood Cliffs, N.J., 1984, pp. 83–86. Plants that exceed the upper or lower statistical thresholds are advanced to the next generation. The statistical threshold chosen will depend upon the population size, the genetic variation known or expected in the population and the desired selection intensity, as is known in the art.

Although a selected plant possesses the heritable trait of altered non-seed glucosinolates, absolute glucosinolate levels will vary depending on growing conditions to some extent. Nevertheless, compared to the starting $P_0$ population, a significant difference in non-seed glucosinolate levels is observed between the $P_0$ population and a plant produced according to the invention.

One or more selected $P_0$ plants are selfed, or crossed to another $P_0$ plant having altered total glucosinolate levels. The choice between selfing or crossing to another $P_0$ plant will to some extent be determined by the species of plants. $P_0$ plants preferably are selfed when using a *B. napus* population or certain *B. campestris* cultivars. As an alternative, a plurality of $P_0$ plants may be identified and such plants may be intermated, i.e., crosses made among the plurality of $P_0$ plants having the same directional alteration in total non-seed glucosinolates.

$P_1$ seeds are replanted and assayed for total non-seed glucosinolate levels as described above and $P_1$ plants having the desired altered glucosinolate level are identified. The statistical threshold for selection of $P_1$ plants typically is as stringent as, or less stringent than, the threshold used in the initial selection.

Progeny of the $P_1$ plant or plants typically undergo further breeding, e.g., selfs, backcrosses, or pedigree selection, to yield a line or cultivar. Breeding to produce a line or cultivar incorporates desired characteristics such as yield, standability, disease resistance and maturity as well as the desired heritable level of total non-seed glucosinolates. Typically, progeny of $P_1$ plants ($P_2$ seed) are grown out and at least one $P_2$ plant inheriting an altered total glucosinolate level is selected as described above. The breeding and selection process is continued in subsequent generations in order to produce a line or cultivar having the trait of heritable reduction in total non-seed glucosinolate levels.

If desired, one or more $P_2$ plants may be outcrossed to a population of Brassicaceae plants different from the $P_0$ population, e.g., a different cultivar, in order to transfer the trait into other cultivars or other species. One or more $P_2$ plant may also be outcrossed to plants of a different Brassicaceae species, e.g., a selected *B. campestris* plant may be crossed to *B. napus*. In addition, backcross or pedigree selection methods may be used in order to confer additional desirable agronomic traits into a line.

In an embodiment of the invention, a polymorphic genetic marker that is genetically linked to altered total non-seed glucosinolate levels may be used to identify or select a plant to be used in subsequent crosses. The use of such markers, often termed "marker-assisted selection", facilitates the selection process by increasing the likelihood that the observed glucosinolate phenotype is due to the underlying heritable genetic trait. Types of markers that are suitable for marker-assisted selection are known in the art and include, without limitation, genomic probes such restriction fragment length polymorphisms (RFLPs) or PCR-based polymorphisms, single-stranded conformational markers (SSCPs), denaturing gradient gel electrophoresis markers (DGGEs), random amplification polymorphism DNA (RAPDS) and microsatellite markers. Aguade, M., W. Myers, A. D. Long, and C. H. Langley, Proc. Natl. Acad. Sci. USA 91:4658–4662 (1994); Rafalski, J. A., and S. V. Tingey, Trends in Genet. 8:275–280 (1993); Lessa, E. P. and G. Applebaum, Molec. Ecol. 2:119–129 (1993); Konieczny, A. and F. Ausubel, Plant J. 4:403–410 (1993).

An illustrative example of a suitable polymorphic marker for selection in Brassicaceae is cosmid g6842, which carries an Arabidopsis genomic DNA fragment from chromosome 2. Lister, C. and Dean, C., Plant J. 4:745–750 (1993). Another useful polymorphic marker is contained in cosmid pCITd23, which is located on chromosome 4. Lister, C. and Dean, C., supra. Other polymorphisms may be present in cosmids g6842 or pCITd23 which are useful for marker-assisted selection in populations other than *A. thaliana*. Furthermore, polymorphisms located outside of the polymorphisms present in g6842 or pCITd23, but genetically linked to g6842 or pCITd23 polymorphisms are suitable for use in the invention. In general, polymorphic markers useful in the invention are within about 25 centiMorgans (cM) of the altered total glucosinolate trait, preferably within about 15 cM, more preferably within about 5 cM of the trait.

Other useful markers include nucleic acids having substantial sequence similarity to the g6842 or pCITd23 fragments. Such nucleic acids typically are substantially similar to about 50 nucleotides or more of a polymorphic sequence in g6842 or pCITd23. Nucleic acids having substantial sequence similarity may be identified by their ability to hybridize to probes in g6842 or pCITd23. Hybridization to identify nucleic acids having substantial sequence similarity may be carried out under stringent conditions as described in widely recognized protocols. See, e.g., Sambrook et al, *Molecular Cloning: A Laboratory Manual* (2nd Edition), Cold Spring Harbor Laboratory Press (1989), pp. 1.101–1.104; 9.47–9.58 and 11.45–11.57. Generally, high stringency conditions reflect at least one wash of the hybridization membrane in 0.05× to 0.5×SSC with 0.1% SDS at 65° C., or washing conditions of equivalent stringency.

Markers polymorphic in a first population may not be polymorphic in a second, different Brassicaceae population.

Methods are known in the art for identifying polymorphisms useful in the second population based on their association with a polymorphism useful in the first population. For example, genomic DNA from the second population can be digested with different restriction enzymes than those used with the first population. A PCR-based polymorphic marker from the first population may be cloned and the cloned fragment tested as an RFLP probe with the second population. Another procedure for obtaining polymorphisms uses bulked segregant analysis to identify a one or more additional RAPD markers linked to the first RAPD marker. The additional RAPD markers can be tested directly in the second population or can be cloned and the cloned fragment tested as an RFLP or PCR-based marker in the second population. Michelmore, R. et al., Proc. Natl. Acad. Sci. USA 88:9828–9832 (1991).

In another embodiment of the invention, a population of $P_0$ Brassicaceae plants is assayed for an increased level of myrosinase enzyme activity in non-seed tissues, preferably cotyledon or leaf tissues. A suitable $P_0$ population comprises plants as described above for total non-seed glucosinolate selection. For example, a $P_0$ population may comprise plants derived from mutagenized seeds. Alternatively, a $P_0$ population may comprise plants genetically engineered for increased myrosinase activity, e.g., having a recombinant DNA construct expressing a myrosinase coding sequence. Chadchawan, S., et al., Plant Phys. 105:671–672 (1993). Such constructs typically include regulatory sequences such as a promoter and enhancer sequences for high level expression, preferably in non-seed tissues.

Selection for increased levels of myrosinase is carried out in a manner similar to that described above for glucosinolate levels, e.g., at the $P_0$, $P_1$, and, optionally, $P_2$ and subsequent generations. Assays for myrosinase levels may be carried out by methods known in the art, for example, removing endogenous glucosinolates and measuring myrosinase enzyme activity spectrophotometrically. As discussed above for glucosinolate assays, myrosinase assays preferably are carried out and completed before flower emergence, so that a plant or plants having the desired myrosinase activity level are identified before pollinations are made. Statistical thresholds for selecting plants having increased myrosinase activity are determined based on the population size, genetic variation in the population and selection intensity that is applied, as discussed above.

Plants developed by a method of the invention may be any species of the family Brassicaceae. Preferred species include the spring and winter forms of *Brassica campestris* and *Brassica napus*.

In another embodiment of the invention, a population of $P_0$ Brassicaceae plants are used to select for a plant carrying both the trait of altered total non-seed glucosinolate level and the trait of increased myrosinase activity.

The inventors have found that plants having heritable alterations in total non-seed glucosinolate levels show significantly reduced susceptibility to leaf feeding by adult and larval forms of cruciferous insect pests of Brassicaceae. Cruciferous insects include flea beetles, diamond back moths and cabbage butterflies. Leaf damage may be reduced by more than 10% compared to control plants. Similarly, populations inheriting an increased level of myrosinase, or increased levels of both total non-seed glucosinolates and myrosinase activity, show decreased susceptibility to leaf damage by coleopteran insect pests of Brassica. Such damage may be reduced by more than 10% compared to control plants.

Plants of the invention are advantageous in that alterations in glucosinolate levels or myrosinase levels, or both, reduce insect damage compared to plants of the $P_0$ population. Many cruciferous insects, including diamond back moths, flea beetles and cabbage butterflies prefer to feed on young seedlings, resulting in yield losses and requiring the use of insecticides to control insect damage. Plants produced according to the invention can respond more vigorously to insect attack, resulting in higher plant counts in the field and increased yield relative to $P_0$ plants. Moreover, such plants can reduce the use of insecticides, thereby lowering the cost of production for farmers.

Plants produced according to the invention are advantageous in that such plants may now be grown in areas where high insect populations preclude the use of rape, canola, or turnip rape as a crop. Moreover, a reduction in insect leaf or cotyledon feeding leads to less physiological stress on plants, which results in more consistent seed quality traits, such as oil and protein produced from such seeds. Plants according to the invention are more likely to mature at the expected time, resulting in less chlorophyll in seeds, and to higher oil quality.

Because genetic control of glucosinolate levels in cotyledons and leaves is separable from levels in seeds, insect damage to non-seed tissues can be reduced by methods of the invention while maintaining low glucosinolate levels in canola quality rape seeds.

The invention will be further understood with reference to the following illustrative embodiments, which are purely exemplary, and should not be taken as limiting the true scope of the present invention as described in the claims.

EXAMPLES

Example 1

Selection for altered glucosinolate levels

Seeds from a wild population of *B. rapa* were collected in the Bitterroot Valley, Montana. Seeds from 45 plants in the wild population were collected and pooled. This bulk seed collection was used to select for high or low total non-seed glucosinolate concentrations. The selection experiment was started with 500 seedlings, which population size is sufficient to minimize genetic drift and inbreeding effects.

*B. rapa* is an outcrossing species, which minimizes the effects of linkage disequilibrium. Crow, J. and Kimura, M., *An Introduction to population Genetics Theory*, Burgess Publishing, Minneapolis, Minn., Chapter 2. Linkage disequilibrium refers to statistical dependence between genotype frequencies at two loci and can cause genotypes to have correlated values for two traits even when there is no causal or functional relationship between these traits. Linkage disequilibrium can confound the effects of many loci, particularly in wide crosses, e.g., interspecific crosses. Young, N. and Tanksley, S., Theor. Appl. Genet. 77:353–359 (1989); Giamoustaris, A. and Mithen, R., Ann. Appl. Biol. 126:347–363 (1995). Consequently, results from studies involving wide crosses can be difficult to interpret.

Total glucosinolate levels in cotyledons were correlated with total glucosinolate concentrations in true leaves (glucosinolates: r=0.37, 104 plants, P=0.001; myrosinase: r=0.72, 104 plants, P<0.001). Selection was conducted on cotyledons because cotyledons were more easily handled for the hundreds of assays required in the selection experiments.

Total non-seed glucosinolates were measured by a protocol similar to that described by Heaney, R. and Fenwick, G., Z. Pflanzenzuchtung 87:89–95 (1981). Mini-columns were prepared from 1.2 ml polypropylene tubes by making a small hole in the bottom of each tube with a heated inoculating needle. The hole was made by forcing the needle from the inside out to promote proper drainage. A small amount of glass wool was then packed into the bottom of each column. DEAE Sephadex®-A25 (Pharmacia) was hydrated overnight in excess distilled $H_2O$ ($dH_2O$). The excess $H_2O$ was decanted from the Sephadex® slurry and, using a disposable pipet with an enlarged tip, 400 µl of slurry was dispensed into each column and allowed to drain. Each column had a bed volume of 200 µl.

Each column was washed once with 1 ml of 0.5M pyridine acetate (19.8 ml pyridine+15 ml glacial acetic acid, brought to 500 ml with $dH_2O$) and twice with 1 ml of $dH_2O$, allowing the column to drain between each aliquot. If not used immediately, columns were stored at 40° C. with column tips immersed in a small amount of $dH_2O$.

One cotyledon was removed from a 7 day old plant and the cotyledon was scanned under a desktop computer scanner (Hewlett-Packard) linked to a personal computer. Cotyledon area was determined by a computer program that counted pixels in the scan; the data were stored in a computer file. Each cotyledon was placed in a 1.2 ml tube containing 0.5 ml dH2O and four 3/32 inch ball bearings. Tubes were placed in a 96 well format rack having holes in the bottom and sides of the rack. The rack and tubes were placed in a glycerol bath and incubated at 100°–1050° C. for 5 minutes. No more than 64 tubes were heated at one time, avoiding the use of wells at the center of the rack. The rack and tubes were then placed in ice water to cool. After cooling, the tubes were transferred to a centrifuge rack, capped securely and agitated on a paint shaker for at least 45 seconds to macerate the cotyledon. A lead acetate-barium acetate solution (0.5 ml, 0.3M each lead acetate and barium acetate in 0.29% v/v glacial acetic acid in $dH_2O$) was added to the macerated extract and the tubes were mixed. The extract was then centrifuged at 3200 rpm for 10 minutes.

An aliquot of the extract (250 µl) was passed over a charged DEAE Sephadex®-A25 column. Up to about 500 µl of extract can be used, if desired. The column was washed twice with 200 µl of 4M acetic acid, then washed three times with 500 µl of dH2O, draining and discarding the eluate after each wash. The rate of elution can be increased by blotting the tip of the column on a pad of paper towels.

One hundred µl of myrosinase (0.645 U/ml, 3 mg/ml, from *Sinapis alba*, Sigma Chemical Co.) were added to each column. Columns were covered and incubated overnight at room temperature. Following the myrosinase incubation, each column was washed with 750 µl $dH_2O$ and the eluate, containing the glucose reaction product, was collected in a 1.2 ml tube.

An equal volume (200 µl) of each eluate was transferred to a well of a microtiter plate and 100 µl of glucose oxidase/peroxidase color reagent was added to each well. Glucose oxidase/peroxidase color reagent contained equal volumes of reagent #1 and reagent #2. Reagent #1 contained glucose oxidase (13 U/ml), 0.8 mM 4-aminoantipyrine and imidazole buffer, pH 7.0. Reagent #2 contained 2.5 U/ml peroxidase, 8.8 mM phenol and imidazole buffer, pH 7.0. Imidazole buffer contained 0.136M imidazole, pH 7.0, 0.03% w/v sodium azide and 0.42% v/v glacial acetic acid. The microtiter plates were covered and incubated at room temperature for one hour. A standard curve was prepared from wells containing only glucose and wells containing only reagents. After one hour, the absorbance at 490 nm ($A_{490}$) was measured and the data was stored in a computer file.

The $A_{490}$ for each cotyledon was divided by the cotyledon area to obtain a specific glucosinolate level ($A_{490}$ per $mm^2$ leaf or cotyledon). Specific glucosinolate and myrosinase concentrations decrease as seedlings develop (e.g., in the field, specific glucosinolate concentration=4.6–61.6 area+ 250.8 $area^2$; $R^2$=63%; F=50.9; df=2, 60; P<0.001). To correct for variation in seedling development within a population, a developmentally adjusted glucosinolate value was calculated as the residuals from the regression of specific concentration on leaf (or cotyledon) area.

The frequency distribution of developmentally adjusted glucosinolate concentration is shown for the base $P_0$ population in FIG. 1. After eliminating 5% of individuals at each of the low and high extremes to avoid outliers, the 48 highest and 48 lowest individuals were selected and transplanted to a growth room. Plants within each selected group were mass pollinated (random mating within the selected population) to produce $P_1$ progeny. For the next generation of selection, at least four $P_1$ seeds from each high glucosinolate selected $P_0$ plant were planted together in a random design and total non-seed glucosinolate levels determined as described above. At least four $P_1$ seeds from each low glucosinolate selected $P_0$ plant were planted and assayed in the same manner. At least 250 $P_1$ plants were grown per treatment. After calculating the developmentally adjusted glucosinolate level as described above, 5% tails from the frequency distribution were excluded and the 48 highest and 48 lowest plants from the remaining population were selected for advancement to the next generation. Plants within each group were intermated as described above to obtain $P_2$ progeny.

Variance effective population size was approximately 72 (=1.5×48), due to uniform numbers of progeny through the maternal component of fitness (Crow, J. and Kimura, M., supra, p. 358). Therefore, genetic drift was unlikely to be an important factor in these selection experiments.

Figure 2:
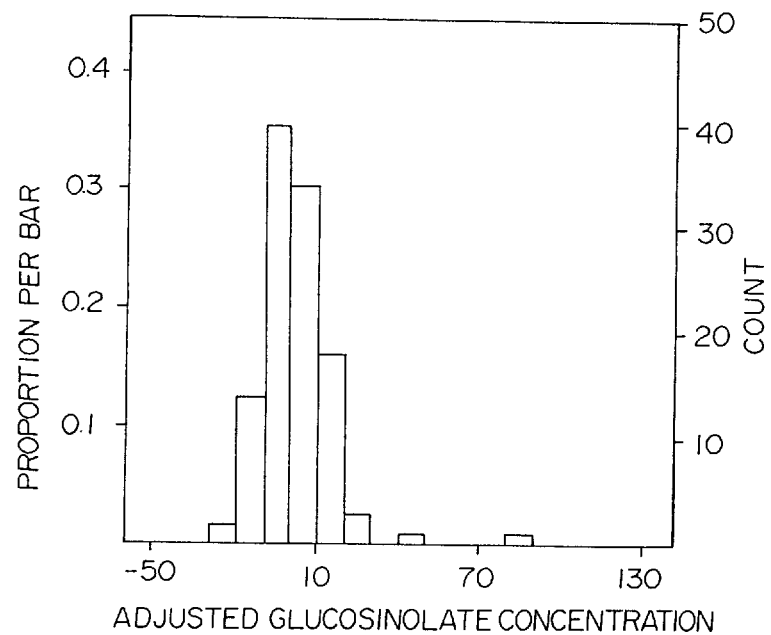
FIG. 2 is a histogram showing the frequency distribution of developmentally adjusted total non-seed glucosinolate levels in a $P_2$ *B. rapa* population after selection for decreased glucosinolate levels.
Figure 3:
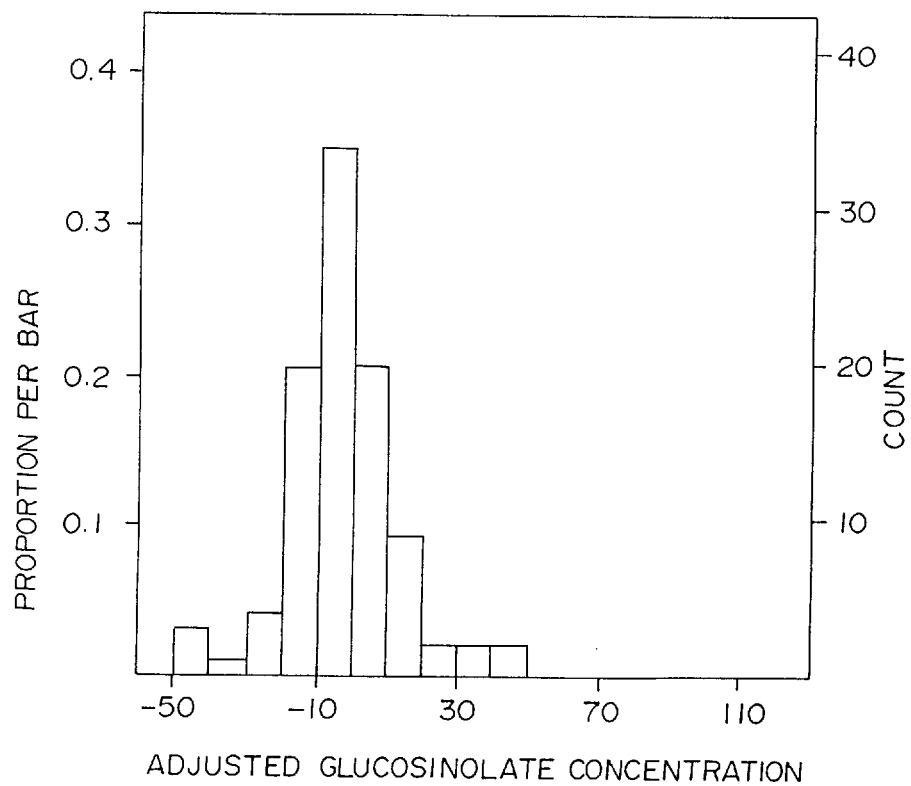
FIG. 3 is a histogram showing the frequency distribution of developmentally adjusted total non-seed glucosinolate levels in a $P_2$ *B. rapa* population after selection for increased glucosinolate levels.

A histogram of developmentally adjusted glucosinolate levels in cotyledons is shown for the low glucosinolate-selected $P_2$ population in FIG. 2 and for the high glucosinolate-selected $P_2$ population in FIG. 3. The results indicated that there were statistically significant differences between high and low populations after only two generations of selection. ANOVA results were: $r^2$=6.0%; F=11.36; df=1,3; P=0.043. High and low populations differed from each other by about ½ standard deviation. Statistically significant heritabilities were calculated from parent-offspring regressions ($h^2$=2[slope] for half sibs; ANOVA: $h^2$=0.17; F=4.75; df=1,208, P=0.03). Falconer, D., *Introduction to Quantitative Genetics,* 3rd ed., Wiley, N.Y., 1989. These results indicate that increased and decreased levels of total non-seed glucosinolate are heritable traits that can be selected for in Brassicaceae plants.

A field experiment with the two glucosinolate-selected populations was conducted near Corvallis, Oregon, about 16 km from the site where the $P_0$ seeds were originally collected. $P_2$ seeds from high and low populations were planted in a randomized manner within each of 10 blocks. Each block contained a total of 96 seeds, 48 seeds from each selection treatment. Each block also contained two border rows of non-experimental plants to control for edge effects. Seeds were planted 4 cm apart to control for competitive effects. Seeds planted in the field were first germinated in the laboratory. If seeds from selected plants did not germinate, or if selected plants produced too few seeds for adequate replication, their position in the blocks were filled with non-experimental seed to keep competitive effects uniform. Lack of germination or seed shortages reduced the number of experimental seeds by approximately 20 seeds per block. These effects were approximately equal between high and low selected lines (P>>0.05). There were approximately 760 $P_2$ seeds planted in the experiment.

A whole block factor of nitrogen fertilizer was added to investigate a potential genotype-by-environment interaction. Fertilizer was added to half the blocks at random in each experiment. Before planting, a mixed sampling of soil nitrates from the field showed nitrate levels to be 65.23 g/m$^2$. Urea (46% N) was added at 4.68 g per 0.26 m$^2$ block just before planting, which increased soil nitrogen levels to 195.00 g/m$^2$. Increasing soil nitrogen levels increases foliage nitrogen levels in *B. rapa* at this site. Jackson, G., et al., Montana AgResearch 10:21–24 (1993).

Thus, in the field, blocks were nested within nitrogen levels and high and low selection treatments were randomized within each block. This constitutes a split plot design, with nitrogen treatment cross-classified with selection treatment.

Herbivory by flea beetle adults was assessed by counting the number of uniform pits chewed per leaf on cotyledons and on the first true leaf. Pit counts were divided by leaf size (width for cotyledons, length for true leaves) to obtain a damage estimate per cotyledon or leaf area for each plant. Cotyledon width was also used as a covariate in statistical analyses to further control for developmental changes in metabolite concentrations.

Herbivory by specialist lepidopteran larvae (diamondback moth and cabbage butterfly) was estimated on a visual scale from 0 to 5 on adult plants at the time most plants began flowering, with 0 representing no insect damage and 5 representing maximum insect damage. Three observers were used to estimated herbivory. Only one observer estimated herbivory within a particular block, to avoid within-block observer bias.

When fruits were fully developed, the number of fruits and average fruit length from three fruits that were four, five, and six nodes down on the main inflorescence were recorded. The number of pods multiplied by the average pod length was used as an estimate of seed production per plant. Estimated seed production was taken as an estimate of the female component of fitness for each plant.

Data were analyzed with a computer statistics program (SYSTAT, Evanston, Ill.). Response variables were log transformed before analysis if needed to comply with assumptions of normality. Residuals were examined for homoscedasticity.

The herbivory data are summarized in Tables 1 and 2. The difference between genotypes in each environment was statistically significant (P=0.039).

TABLE 1

Herbivory by flea beetles on glucosinolate populations

| Selected Population | Mean Pit Number | P value |
|---|---|---|
| High Gluc. | 0.95 +/- 0.036 | 0.040 |
| Low Gluc. | 0.86 +/- 0.037 | |

[a]Blocks with added soil nitrogen.

TABLE 2

Herbivory by Lepidopteran larvae on glucosinolate populations

| Selected Population | Mean Score |
|---|---|
| High | 1.29 +/- 0.11 |
| Low | 1.36 +/- 0.11 |
| High + N[a] | 1.56 +/- 0.10 |
| Low + N[a] | 1.34 +/- 0.12 |

[a]Blocks with added soil nitrogen.

Statistically significant differences in levels of flea beetle herbivory were found between the high and low glucosinolate populations (13% difference in leaf area consumed, p=0.01 by ANOVA). In the absence of added soil nitrogen, the high glucosinolate population showed a 9.8% higher levels of herbivory (Table 3). This difference was statistically significant in cotyledons (P=0.040). In true leaves there was a significant effect of nitrogen (P=0.026; Table 4); plants in blocks with added nitrogen had 28.6% lower levels of herbivory.

For lepidopteran larvae there was a statistically significant interaction between nitrogen and glucosinolate selection treatment in the glucosinolate field experiment (P=0.039; Table 4). In blocks with added nitrogen, the population selected for low glucosinolate concentrations had 16% lower herbivory, whereas in the absence of added soil nitrogen, the low glucosinolate population had 5% higher herbivory. These results indicate a significant genotype-by-environment interaction (GxE).

Although populations having low total glucosinolate concentrations showed reduced leaf and cotyledon feeding by flea beetles, there was no significant difference in fitness between low and high selection treatments (P=0.056; Table 4).

TABLE 3

| Population | Glucosinolate Concentration | Herbivory |
|---|---|---|
| High Glucosinolate | 100.0 +/- 3.0 | 100.0 +/- 3.8 |
| Low Glucosinolate | 84.2 +/- 2.9 | 90.2 +/- 3.8 |

TABLE 4

ANOVA tables from split-plot field experiment for high and low glucosinolate-selected populations were compared for resistance and fitness parameters. Block {N} is the variation among blocks nested within the nitrogen (N) factor; Selection (S) is the variation between high and low selected populations; size is the covariate, cotyledon width.

F ratios[a]

| Source | df | Cotyledon resistance to flea beetles | Leaf resistance to flea beetles | Leaf resistance to Lep. larvae | Fitness |
|---|---|---|---|---|---|
| Nitrogen | 1 | 0.14 | 7.45* | 0.28 | 0.93 |
| Block {N} | 8 | 18.68*** | 10.64*** | 4.38*** | 18.54*** |
| Selection (S) | 1 | 6.00** | 0.13 | 1.67 | 5.00 |
| N*S | 1 | 0.26 | 0.52 | 6.10* | 0.00 |
| S*Block {N} | 8 | 1.09 | 1.23 | 0.29 | 1.648 |

TABLE 4-continued

ANOVA tables from split-plot field experiment for high and low glucosinolate-selected populations were compared for resistance and fitness parameters. Block {N} is the variation among blocks nested within the nitrogen (N) factor; Selection (S) is the variation between high and low selected populations; size is the covariate, cotyledon width.
F ratios[a]

| Source | df | Cotyledon resistance to flea beetles | Leaf resistance to flea beetles | Leaf resistance to Lep. larvae | Fitness |
|---|---|---|---|---|---|
| size | 1 | 0.93 | 6.69** | 4.48* | 159.19*** |
| ERROR | 476[s] | 0.19 | 0.03 | 1.59 | 0.438 |

[a]Mean square (MS) for F ratios and corresponding degrees of freedom (df) in split-plot design as specified in Steel, J. and Torrie, J., Principles and Procedures of Statistics: A Biometrical Approach, 2nd ed., McGraw-Hill, New York (1980).
[s]df for MS ERROR ranged from 476 to 544
*P<0.05; P<0.01; *P<0.001

Example 2

Selection for altered myrosinase levels

Seeds from the base population of Example 1 were used to select for plants having altered levels of myrosinase. A pool of 500 $P_0$ seeds was planted in the greenhouse and a cotyledon was removed from each plant for myrosinase assays. In the myrosinase assay, endogenous glucose and glucosinolates were removed and myrosinase collected through a desalting G-25 or G-50 Sephadex® column. An exogenous glucosinolate was added (sinigrin) and the resulting rate of glucose production was measured spectrophotometrically.

Excess $dH_2O$ was decanted from Sephadex® G25 or G50 that had been hydrated overnight, using an Eppendorf repeater pipet equipped with a syringe with an enlarged tip opening. About 300 μl of Sephadex slurry was transferred to each well of a Silent Monitor™ 96 well membrane test plate (Product NO. SM300LP, Pall Corporation) to form a Sephadex® mini-column. These plates contain 3 micron Loprodyne® membrane bottomed wells. Only wells 1–80 of each plate were used for extracts; wells 81–96 were reserved for controls and a glucose standard curve. The prepared plates can be prepared one day before use, covered with Parafilm®, and stored at 40° C. Immediately before use, all excess dH2O was removed from the mini-column plates by placing the plate over an empty 96 well microtiter plate and centrifuging in a Hermle Z320 centrifuge at 1000 rpm.

An extract from each cotyledon was prepared by placing the cotyledon in a 1.2 ml tube containing four 3/32 inch ball bearings and adding 750 μl of 200 mM Tris HCL, pH 7.5. In some experiments, extraction buffer also contained 10 mM EDTA and 2 mM DTT. Tubes were place in a 96 well rack having holes in the bottom and sides of the rack. The tubes were capped securely and agitated on a paint shaker for at least 45 seconds to macerate the cotyledon. One hundred μl of macerated extract were transferred to a mini-column well. Each extract and Sephadex® mixture was stirred gently with a pipet tip. The mixture was allowed to equilibrate for 5 minutes at room temperature.

The mini-column plate then was placed over an empty 96 well microtiter plate and the two plates were taped together and centrifuged in a clinical centrifuge. To collect the eluate in the microtiter plate, the centrifuge was allowed to reach 600 rpm and then immediately shut off. The tape was removed and the eluate-containing microtiter plate was set aside. The mini-column plate was washed with 50 μl of $dH_2O$ per well for G-25 columns or with 25 μl of $dH_2O$ for G-50 columns. The mini-columns were not stirred during the $dH_2O$ wash. After 5 minutes, the mini-column plate and the microtiter plate were taped together in the same configuration and centrifuged as described above to collect the second eluate. The volume of the combined eluates was about 100 μl. It is important to centrifuge no faster than 600 rpm, since centrifugation at higher speeds causes the column packing material to become "dry" and increases the amount of background glucose in the eluate.

Serial dilutions of a glucose standard (1 mM to 0.0625 mM glucose, 100 μl per well) were added to wells 81–85 and 89–93. Reagent blanks (100 μl) were added to wells 86–88 and 94–96. Positive control microtiter plates contained serial 2-fold dilutions of commercial myrosinase (100 μl per well; 2 mg/ml, 0.43 U/ml at the highest concentration) instead of sample eluate. Negative control plates were prepared by adding 25 μl of sodium phosphate (33 mM, pH 6.5) to sample wells instead of the sinigrin substrate.

The myrosinase reaction was started by adding 25 μl of sinigrin (5 mM, Sigma) to each well of experimental sample plates and positive control plates. Equal volumes of color reagents #1 and #2 from Example 1 were mixed and 50 μl of the mixture was added to each well. The microtiter plate was covered with Parafilm® and incubated at room temperature for 60 minutes. The Parafilm® was then removed, each well was mixed for 10 seconds and the $A_{490}$ measured in a BioRad Microplate Reader. The data was stored in a computer file.

Figure 4:
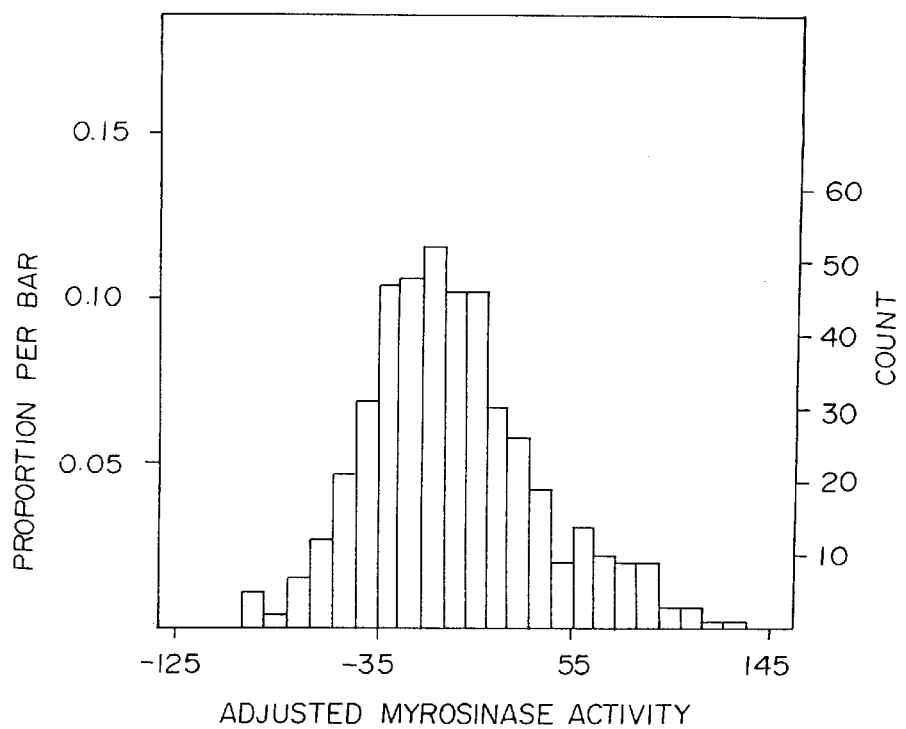
FIG. 4 is a histogram showing the frequency distribution of developmentally adjusted myrosinase activity in a $P_0$ *B. rapa* population.

The $A_{490}$ for each cotyledon was divided by the cotyledon area to obtain a specific myrosinase activity ($A_{490}$ per $mm^2$ leaf or cotyledon). A developmentally adjusted myrosinase activity was calculated in the same manner as described for glucosinolates in Example 1. The frequency distribution of developmentally adjusted myrosinase activity is shown for the base $P_0$ population in FIG. 4.

After eliminating 5% of individuals at each of the low and high extremes to avoid outliers, the 48 highest and 48 lowest individuals from the $P_0$ population were selected, transplanted and randomly mated within selected groups as described in Example 1. After harvest, at least four $P_1$ seeds from each high and low myrosinase-selected $P_0$ plant were planted together in a random design and myrosinase activity determined as described above. At least 250 $P_1$ plants were grown per treatment. After calculating a developmentally adjusted myrosinase activity in the same manner as described above, 5% tails from the frequency distribution were excluded and the 48 highest and 48 lowest plants from the remaining population were selected for advancement to the next generation. Plants within each group were intermated as described above to obtain $P_2$ progeny.

Figure 5:
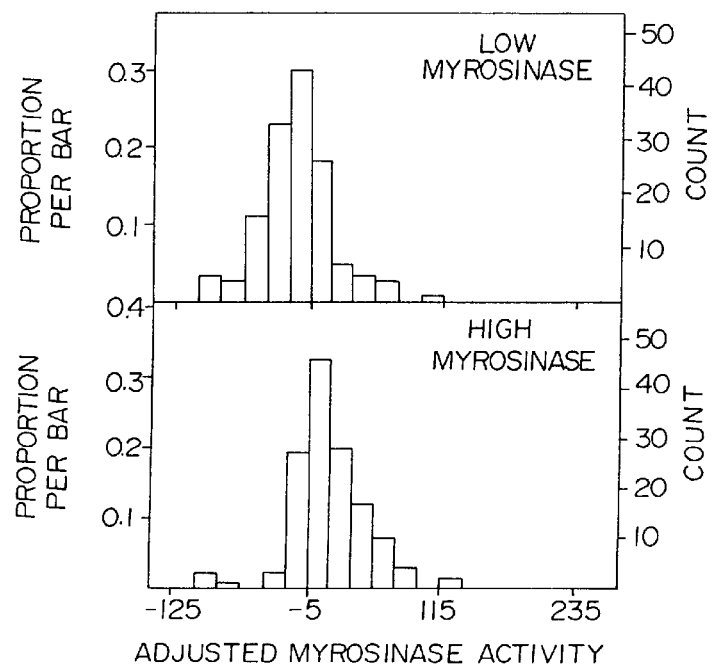
FIG. 5 is a histogram showing the frequency distribution of developmentally adjusted myrosinase activity in two $P_2$ *B. rapa* populations selected for decreased (upper histogram) or increased (lower histogram) myrosinase activity.

Histograms of the high and low myrosinase-selected $P_2$ populations are shown in FIG. 5. The results indicate that there were statistically significant differences between high and low populations after two generations of selection (ANOVA:$r^2$=18.3%; F=22.12; df=1,4; P=0.009). High and low populations differed by about two standard deviations in the myrosinase selection experiment. The high population would be expected to differ from the base population by about one standard deviation, assuming that the mean of the base population lies halfway between the means of the high and the low population. Statistically significant heritabilities were calculated from parent-offspring regressions ($h^2$=2 [slope] for half sibs) (Myrosinase: $h^2$=0.35; F=20.95; df=1, 308; P<0.001).

A field experiment with the high and low myrosinase-selected populations was carried out at the same time and at the same site as the field experiment of Example 1. genotypes were planted in the field in a randomized design, and scored for insect herbivory. $P_2$ seeds were planted in the same split plot design as described in Example 1. Lack of germination or seed shortages reduced the number of experimental seeds by approximately 12 seeds per block. These effects were approximately equal between high and low selected lines. For the 10 blocks planted in each experiment, there were about 840 experimental seeds planted in the myrosinase experiment.

Herbivory and fitness were measured as described in Example 1. Data were analyzed as described in Example 1. The herbivory data are summarized in Table 5.

TABLE 5

Herbivory by Flea Beetles on Myrosinase Populations

| Myrosinase Population | Mean Pit Number |
|---|---|
| High | 0.69 +/- 0.02[a,*] |
| Low | 0.78 +/- 0.02[a,*] |

[a](+/- 1 Standard Error)
*Statistically significant, P = 0.043

Figure 6:
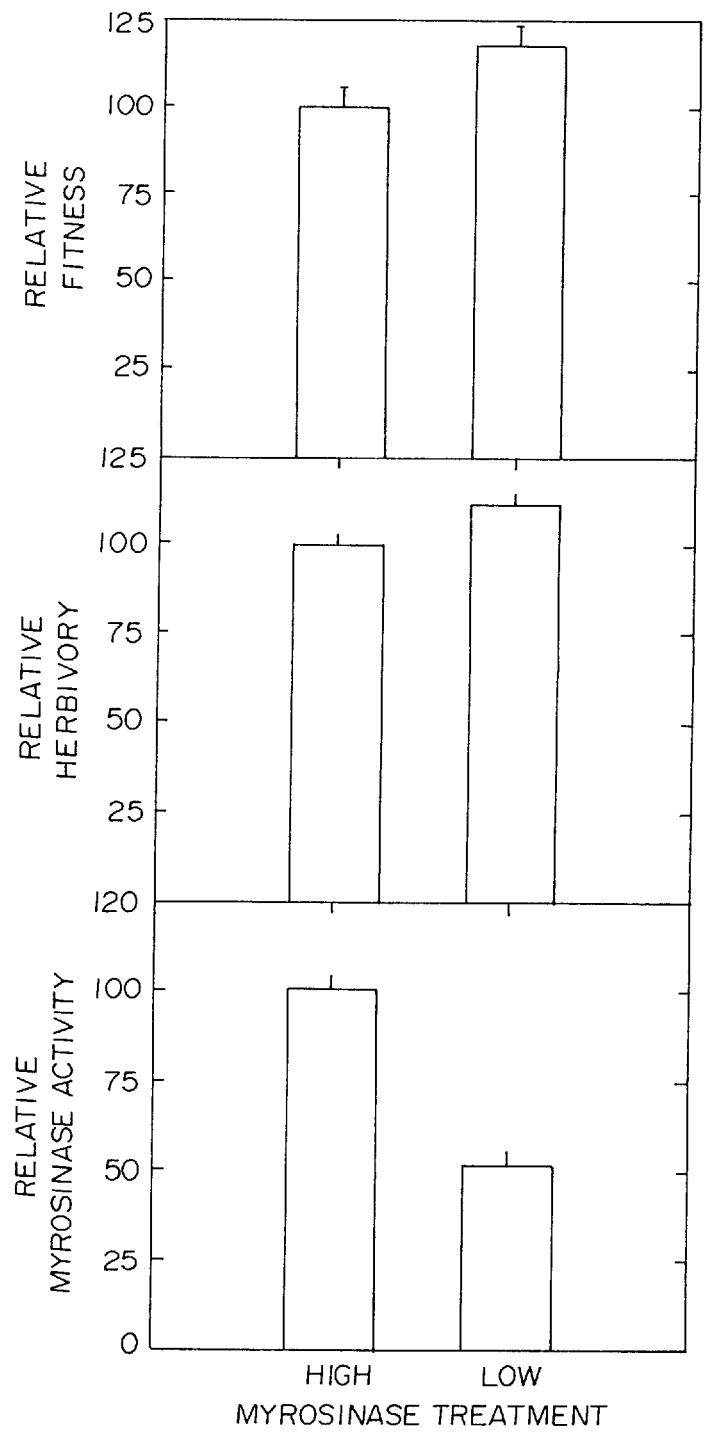
FIG. 6 is a bar graph comparing the fitness, herbivory and myrosinase activity for the two $P_2$ *B. rapa* populations of FIG. 5. The fitness, herbivory and myrosinase activity values for the increased myrosinase-selected population were each set at 100 and the corresponding values for the decreased myrosinase-selected population determined.

In the field, the population selected for increased myrosinase activity was 10.3% more resistant than the low myrosinase line to flea beetles (FIG. 6, Table 5). This difference in resistance to flea beetles between high and low populations was statistically significant (P=0.043; Table 6), and was only found to be significant for feeding on true leaves.

Plant fitness was 15.5% lower in the population selected for high myrosinase concentrations (FIG. 6). This difference in the female component of fitness was statistically significant (P=0.016; Table 6).

Resistance to specialized lepidopteran larvae was not affected by selection for altered myrosinase activity. Instead, added nitrogen increased herbivory by 59% compared to the ambient nitrogen levels (P=0.011; Table 6). No interaction between nitrogen and selection treatment was detected.

TABLE 6

ANOVA tables from split-plot field experiments for myrosinase in which high and low selected populations were compared for resistance and fitness parameters. Block {N} is the variation among blocks nested within the nitrogen (N) factor; Selection (S) is the variation between high and low selected populations; size is the covariate, cotyledon width.
F ratios[a]

| Source | df | Cotyledon resistance to flea beetles | Leaf resistance to flea beetles | Leaf resistance to Lep. larvae | Fitness |
|---|---|---|---|---|---|
| Nitrogen | 1 | 3.97 | 0.33 | 11.02** | 0.19 |
| Block {N} | 8 | 30.27*** | 2.41* | 6.80 | 13.31*** |
| Selection (S) | 1 | 0.56 | 5.76* | 1.67 | 9.22* |
| N*S | 1 | 0.23 | 0.01 | 0.03 | 0.44 |
| S*Block {N} | 8 | 1.39 | 0.84 | 1.82 | 0.75 |

TABLE 6-continued

ANOVA tables from split-plot field experiments for myrosinase in which high and low selected populations were compared for resistance and fitness parameters. Block {N} is the variation among blocks nested within the nitrogen (N) factor; Selection (S) is the variation between high and low selected populations; size is the covariate, cotyledon width.
F ratios[a]

| Source | df | Cotyledon resistance to flea beetles | Leaf resistance to flea beetles | Leaf resistance to Lep. larvae | Fitness |
|---|---|---|---|---|---|
| size | 1 | 1.94 | 35.88*** | 25.52*** | 151.40*** |
| ERROR | 527[s] | 0.04 | 0.14 | 0.764 | 0.44 |

[a]MS for F ratios and corresponding df in split-plot design as specified in Steel, R. and Torrie, J., supra.
*P<0.05; P<0.01; *P<0.001
[s]df for ERROR ranged from 527 to 747

Example 3

Selection for altered glucosinolate levels and myrosinase activity in *Arabidopsis thaliana*

Phenotypic analyses of total non-seed glucosinolate levels, myrosinase activity and insect leaf damage were carried out on homozygous recombinant inbred lines of *Arabidopsis thaliana*. The lines were derived from a cross between ecotypes Columbia and Landsberg erecta. Lister, C. and Dean, C., Plant J. 4:745–750 (1993). The lines were obtained from the Arabidopsis Biological Resource Center (Columbus, Ohio). Thirty-nine lines were grown in a randomized complete block design with 80 plants per flat in 4 flats. Three weeks after planting, glucosinolate concentrations were measured on a true leaf from each plant as described in Example 1. Leaf areas were determined by computer scanning as described in Example 1. Specific total non-seed glucosinolate levels were calculated in units proportional to glucosinolate level per $mm^2$ leaf area. The mean specific glucosinolate level for each of 38 recombinant inbred lines is shown in Table 7.

TABLE 7

Glucosinolate Levels and Myrosinase Activity for Arabidopsis Recombinant Inbreds.

| RI LINE | ADJ GS | Myrosinase |
|---|---|---|
| 5 | 0.769 | 0.772 |
| 13 | -0.390 | -0.387 |
| 14 | 0.672 | -1.109 |
| 17 | 0.379 | -0.800 |
| 25 | -0.220 | -0.317 |
| 30 | -0.820 | 0.319 |
| 32 | -0.398 | -0.249 |
| 33 | 0.643 | -0.946 |
| 34 | -0.263 | -0.153 |
| 46 | 0.169 | -0.188 |
| 62 | 0.352 | 0.090 |
| 67 | 0.275 | 0.688 |
| 79 | -0.011 | 0.175 |
| 90 | 0.292 | -0.567 |
| 107 | 0.038 | -0.413 |
| 113 | 0.353 | -1.099 |
| 115 | 0.247 | -0.546 |
| 160 | -0.625 | -0.195 |
| 167 | -0.334 | -0.277 |
| 180 | -0.130 | -0.069 |

TABLE 7-continued

Glucosinolate Levels and Myrosinase Activity
for Arabidopsis Recombinant Inbreds.

| RI LINE | ADJ GS | Myrosinase |
|---|---|---|
| 194 | −0.601 | −0.773 |
| 232 | N/D | 0.260 |
| 235 | 0.280 | 1.176 |
| 238 | 0.040 | 1.013 |
| 263 | −0.078 | 1.132 |
| 264 | −0.788 | 1.432 |
| 288 | 0.153 | 0.214 |
| 295 | 0.176 | −0.122 |
| 296 | 0.465 | −0.250 |
| 342 | 0.623 | −0.086 |
| 345 | −0.709 | −0.341 |
| 350 | −0.539 | 0.229 |
| 358 | −0.308 | 1.568 |
| 363 | −0.065 | −0.062 |
| 370 | 0.281 | −0.352 |
| 377 | −0.625 | 0.162 |
| 378 | −0.387 | 1.821 |
| 386 | 0.486 | −0.817 |
| 390 | −0.702 | 0.193 |

Myrosinase activity was determined as described in Example 2 on a leaf taken 3 weeks after planting, except that 40 minutes after the enzyme reaction was initiated, $A_{490}$ measurements were taken at 2 minute intervals until the completion of the 60 minute incubation. The velocity of the reaction was determined from the $A_{490}$ measurements and specific myrosinase activity was calculated in units proportional to myrosinase activity per $mm^2$ leaf area. The mean specific myrosinase activity for each of the 39 recombinant inbred lines is shown in Table 7.

Figure 7:
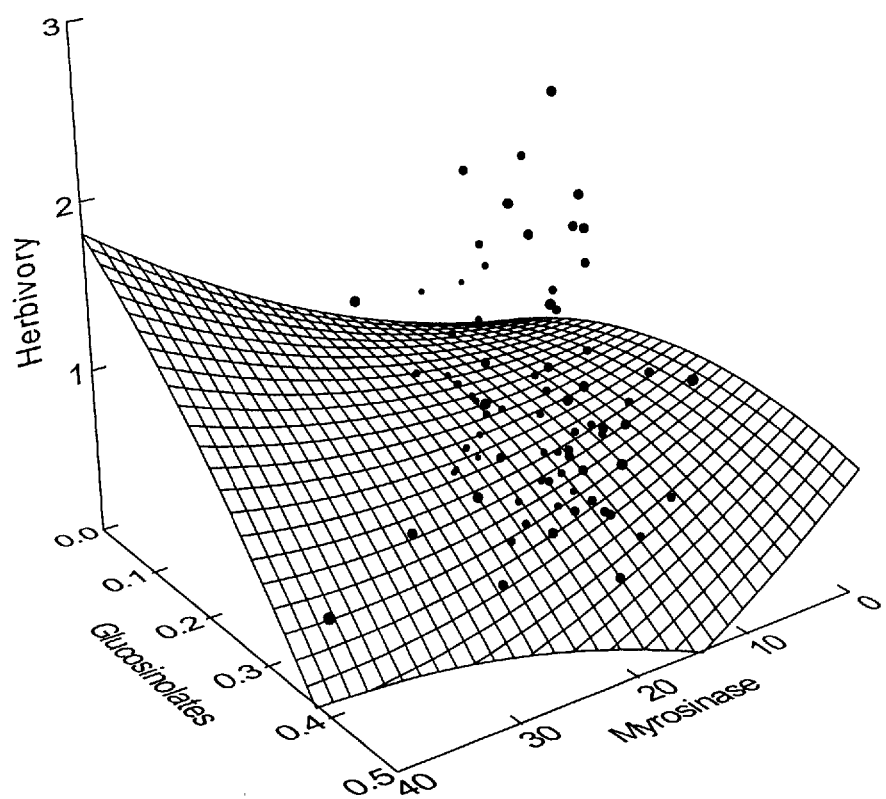
FIG. 7 is a response surface for diamondback moth herbivory, total non-seed glucosinolate levels and myrosinase activity for 39 *Arabidopsis thaliana* homozygous recombinant inbred lines.

One day after removing a leaf for glucosinolate and myrosinase analysis, a single first instar diamondback moth larvae was placed on a leaf of each plant. Leaf tissue consumed (mine size) was scored the following day as described in Example 1, except that a scale of 0 to 3 was used. The data from Table 7 and the mean mine size for each recombinant inbred line were analyzed using quadratic least squares regression to estimate covariant values for the three measurements; the regression analysis is plotted in FIG. 7.

A statistical analysis of the data in Table 7 is presented in Table 8. The results indicate that selecting for increased total non-seed glucosinolate levels and increased myrosinase activity reduces leaf damage by diamond back moth larvae.

TABLE 8

Effects of Glucosinolates and Myrosinase on
Diamondback Moth Larval Feeding
DEP VAR: MINE[a]

| SOURCE | DF | MEAN-SQUARE | F-RATIO | P |
|---|---|---|---|---|
| SpGluc[a] | 2 | 1.062 | 4.547 | 0.027 |
| SpMyr[a] | 2 | 1.156 | 4.948 | 0.021 |
| SpGluc*SpMyr | 1 | 1.768 | 7.568 | 0.014 |
| LeafLen[a] | 2 | 1.392 | 5.960 | 0.012 |
| RI Line | 39 | 0.324 | 1.389 | 0.243 |
| ERROR | 16 | 0.234 | | |

$N = 63$, $R^2 = 80.9\%$
[a]Mine = Insect Score; SpGluc = Area-specific glucosinolate level; SpMyr = Area-specific myrosinase activity; LeafLen = Leaf Length Example 4

Marker-assisted selection of glucosinolate and myrosinase levels

RFLP linkage data for 101 *Arabidopsis thaliana* recombinant inbred (RI) lines, including the 39 lines analyzed for total glucosinolates, myrosinase and herbivory, is shown in Table 9. The data in Table 9 show information for 62 polymorphic markers, including chromosome, map location from an arbitrary starting point on the chromosome (in centiMorgans) and the polymorphic allele present in each RI line. The data are available from the Arabidopsis Biological Resource Center (Columbus, Ohio) and can be downloaded from the AAtDB database on the Internet (http://weeds.mgh.harvard.edu; electronic mail curator@weeds.mgh.harvard.edu).

The marker data from Table 9 and the phenotypic data from Table 7 were analyzed by least squares interval mapping to identify polymorphic molecular markers that were linked to altered myrosinase activity or total non-seed glucosinolate level (Haley, C. S. and Knott, S. A., Heredity 69:315–324 (1992).

One genomic probe, cosmid m105, was found to be linked to altered levels of myrosinase (Table 10). The genomic fragment present in cosmid m105 is located on chromosome 3, approximately 25 map units from the arbitrary zero position at lambda clone m583. Two probes, cosmids g6842 and pCITd23, were found to be linked to altered levels of total non-seed glucosinolates (Table 10). The genomic fragment in cosmid g6842 maps to chromosome 2, approximately 29.2 map units from the zero position at m246. The fragment in pCITd23 maps to chromosome 4, approximately 18 map units from marker g3843.

TABLE 9

The following table contains genetic marker information from the Columbia×Landsberg recombinant inbred lines. A subset of these lines (numbers 5, 13, 14, 17, 25, 30, 32, 33, 34, 46, 62, 67, 79, 90, 107, 113, 115, 160, 167, 180, 194, 232, 235, 238, 263, 264, 288, 295, 296, 342, 345, 350, 358, 363, 370, 377, 378, 386, and 390) were used to map myrosinase activity and glucosinolate concentration quantitative trait loci in this cross, with the least squares interval mapping protocol of Hqaley and Knott (1992). The first paragraph (below) contains the identification number for each recombinant inbred line, in the same order as subsequent paragraphs. Each subsequent paragraph contains the following information; first, the name of the genetic marker, ending with ab asterisk. Second, the chromosome containing this marker (numbered 1 to 5). Third, the location of the genetic marker in centiMorgans. Lastly, the allele for each recombinant inbred line, with "L" indicating the Landsberg allele, "C" indicating the Columbia allele, and "U" indicating unknown.

TABLE 9

```
 4   5  13  14  17 519 619  25  29  30  32  33  34  35  36  37  46  52  53  54
59  62  67  68  71  79  84  90 107 113 115 123 125 131 160 161 166 167 173
175 177 179 180 181 182 188 190 191 193 194 199 209 214 217 231 232 235 237
238 240 242 245 253 257 259 263 264 266 267 279 283 284 288 295 296 297 302
303 311 321 332 342 345 349 350 351 356 358 359 363 367 370 377 378 386 390
394 395 397 398 400 m488*   1  51         L  C  C  L  L  C  U  L  C  C  C  L  C  L  L  C
 H   L       C   C   C   L   L   L   C   C   C   L   L   C   C   U   L   C   L
 C   C   L   L   C   L   L   C   L   C   C   L   L   C   C   U   L   C   L
 C   C   C   C   C   L   L   L   C   L   L   L   L   L   C   L   C   L
 C   C   C   C   L   L   L   L   L   L   C   C   L   L   L   C   L   L   L
 L   C   C   L   C   C   C   C   C
g4715a* 1  55.4       L  C  C  L  L  C  U  L  C  C  C  L  C  L  L
 C   U   L   C   C   C   C   L   L   U   C   C   C   L   L   L   C   C   L
 L   C   C   L   L   C   L   L   C   L   C   C   L   L   C   C   U   L   C
 L   C   C   C   C   L   L   L   C   L   L   L   L   L   L   C   L   C
 L   C   C   C   C   L   L   L   L   L   C   C   L   U   L   C   L   L
 L   L   C   C   L   C   C   C   C   C
g3786*  1  64.5       L  L  L  L  L  C  U  L  C  L  C  L  C  L  C
 C   L   L   C   C   L   L   L   L   L   C   L   L   L   C   L   C   C   L
 L   C   C   L   L   U   L   L   C   L   C   C   L   L   C   C   U   L   C
 L   C   U   C   C   L   L   L   C   L   L   L   C   L   C   L   C
 C   C   C   L   C   L   L   L   C   C   L   U   C   L   U   C   C   L   L
 L   U   C   C   L   C   C   C   C   C
m235*   1  68.5       L  L  C  L  L  C  U  L  C  L  C  L  C  L  C
 C   C   L   L   C   L   C   C   L   L   C   C   C   L   L   C   C   C   C
 L   C   C   L   L   L   L   C   C   L   C   L   C   L   C   U   L   C
 L   L   L   C   C   L   L   L   C   L   C   L   L   C   L   C   L   C
 C   C   C   L   C   L   L   C   C   L   C   L   L   C   C   C   L
 L   L   C   C   L   C   C   L   L   L
g3829*  1  72.5       L  L  L  L  L  C  U  L  C  L  C  L  C  L  C
 C   C   L   U   C   L   C   L   L   U   C   C   U   L   L   C   C   C   C
 L   C   C   L   L   C   C   C   L   C   C   L   C   L   C   U   L
 L   L   L   C   C   L   L   L   C   L   L   L   L   U   U   C   L   C
 C   C   C   C   C   L   L   C   C   L   U   C   L   U   C   C   C   U
 U   L   C   C   L   C   U   U   L   C
m253*   1  82.5       C  L  L  C  L  C  U  L  L  L  L  L   L  L  C
 C   C   L   L   C   C   C   C   L   C   C   C   L   L   C   C   C   C
 L   C   C   C   C   L   C   C   C   L   L   C   L   C   C   L   U   L   C
 L   L   L   C   C   L   L   L   C   L   L   C   L   C   C   L   L   C
 C   C   C   L   L   L   L   C   L   L   C   L   L   C   L   C   L
 H   C   C   C   L   C   L   L   L   L
GapB*   1  92.5       U  C  L  C  U  C  U  L  U  U  L  C  L  U  C
 C   U   L   U   C   C   C   C   U   C   C   U   L   L   C   U   U   U
 L   C   C   C   C   U   U   C   U   L   C   C   L   C   C   L   U   C   L
 L   L   U   U   U   L   C   C   U   U   L   L   L   U   C   U   U   U   U
 C   U   U   U   C   L   L   C   C   C   U   U   C   U   U   C   U   L   U
 C   C   C   U   C   C   U   U   U   L
g4026*  1 110.4       C  C  C  C  L  L  C  C  U  C  C  L  C  L  L
 C   C   L   C   L   C   C   L   C   C   L   L   C   L   C   C   L   L
 C   C   C   C   L   L   C   C   C   C   L   C   L   U   L   C   C   L
 C   C   L   C   C   L   C   C   C   C   C   C   L   C   L   C   L   C   C
 C   C   C   C   C   L   L   H   L
m315*   1 117.4       C  C  C  C  L  L  C  L  C  C  L  C  C  C  C
 C   C   L   L   L   C   C   C   L   C   C   L   C   C   C   C   L   L
 C   C   C   C   L   C   C   C   C   C   C   L   L   C   L   C   C   C
 L   C   C   C   C   L   C   C   C   C   C   C   C   C   L   C   L   C   L
 C   C   C   C   C   C   L   C   L
g4552*  1 119   C  C  C  C  L  C  L  C  C  L  C  C  C  C  C
 C   C   L   L   C   C   C   L   L   C   C   U   C   L   L   C   C
 C   C   C   L   C   C   C   C   C   L   C   C   C   U   C   C   C   C
 C   C   C   L   L   C   C   C   C   C   C   C   L   C   L   C   C   L   L
 L   C   L   C   C   C   L
m532*   1 135.3       L  C  C  C  C  L  U  L  C  L  C  L  C  C  L
 C   C   C   L   L   L   C   C   C   C   C   C   L   C   C   C   C   L   L
 C   C   C   C   L   U   C   C   C   L   C   C   L   C   C   L   U   C   L
 C   C   U   C   C   L   C   C   C   C   C   L   C   C   C   C   C
 C   L   L   C   C   L   L   C   C   C   C   L   C   L   L   L
 L   L   L   C   C   C   C   L
g17311* 1 141   L  C  C  C  C  U  C  L  C  L  C  C  L  C
 C   C   L   L   L   C   C   C   C   C   C   L   C   C   L   C   C   L   C
 C   C   C   C   U   C   C   C   C   C   C   L   C   L   U   C   L   C
 C   U   C   C   L   C   C   L   C   L   C   C   C   L
 L   L   L   L   L   C   L   C   C   C   L   C   L   L   L   L
 L   L   C   C   C   C   L   L
m246*   2  11.1       L  C  C  C  C  L  U  L  L  L  L  L  L  L
```

TABLE 9-continued

| | | | | | | | | | | | | | | | | | | | |
|---|---|---|---|---|---|---|---|---|---|---|---|---|---|---|---|---|---|---|---|
| C | C | L | | C | L | L | L | C | L | L | C | L | L | L | L | L | C | L | C |
| C | L | C | | C | L | L | L | C | L | L | L | L | C | C | L | C | U | L | L |
| C | L | L | | C | L | L | L | L | L | C | C | C | C | L | L | L | L | L | C |
| L | L | L | | L | C | C | L | L | C | L | C | C | C | L | L | C | L | C | L |
| H | L | L | | C | C | L | C | L | L | C | | | | | | | | | |
| g4133* | 2 | 16.2 | | L | C | C | C | C | L | C | L | L | C | L | L | L | L | L | L |
| C | C | L | | C | L | L | L | L | L | L | L | U | U | L | L | C | L | L | C |
| C | L | L | | C | L | L | L | L | L | L | L | C | C | L | C | U | L | L | L |
| C | L | L | | C | L | L | L | L | L | C | C | C | L | L | L | L | L | L | L |
| L | L | L | | C | L | C | L | L | C | L | L | C | L | L | C | C | C | L | L |
| H | L | C | | C | C | L | C | U | C | C | | | | | | | | | |
| g4532* | 2 | 18.5 | | L | C | C | C | C | C | C | L | L | C | L | L | L | L | L | L |
| C | C | L | | U | L | L | L | L | L | L | L | U | U | L | L | L | L | L | C |
| C | L | C | | C | L | L | L | C | L | L | L | L | C | C | L | C | U | L | L |
| C | L | L | | C | L | L | L | L | L | C | C | C | C | L | U | U | L | L | L |
| L | L | L | | C | L | C | L | L | C | L | L | C | L | L | C | L | C | L | L |
| H | L | L | | C | C | L | C | U | L | C | | | | | | | | | |
| g4553* | 2 | 20.4 | | L | C | U | C | C | L | C | L | L | L | L | L | L | L | L | L |
| C | C | L | | C | L | L | L | L | L | L | C | L | L | L | L | L | C | L | C |
| C | L | C | | C | L | L | L | C | L | L | L | L | C | L | C | L | L | L | L |
| C | L | L | | C | L | L | L | L | U | U | C | C | C | L | U | L | L | L | C |
| L | L | L | | C | C | C | L | L | C | L | L | C | L | L | C | L | C | L | L |
| H | L | L | | C | C | L | C | U | L | C | | | | | | | | | |
| m251* | 2 | 47.7 | | L | C | C | C | C | L | U | C | L | L | L | C | L | L | L | L |
| L | C | L | | L | L | L | L | L | L | L | L | L | C | L | C | L | L | L | C |
| C | L | L | | L | L | U | L | C | L | L | L | H | C | C | L | L | U | L | L |
| L | C | U | | C | L | L | L | L | L | C | C | C | L | L | L | L | L | L | L |
| L | L | L | | C | L | C | C | L | C | C | L | C | L | L | L | C | L | L | L |
| C | L | L | | C | C | L | C | L | | | | | | | | | | | |
| er* | 2 | 56.5 | | L | C | C | C | C | U | U | L | L | C | L | C | L | C | L | L |
| C | L | U | | L | U | C | L | U | L | C | C | C | L | C | L | L | C | L | L |
| L | L | L | | L | L | L | L | L | U | L | C | C | L | C | C | L | L | L | L |
| C | C | C | | L | L | L | L | L | L | L | U | L | L | L | L | U | L | L | L |
| C | L | C | | L | L | L | L | C | C | L | U | L | L | L | L | U | L | L | C |
| L | L | C | | C | L | L | L | C | L | | | | | | | | | | |
| g6842* | 2 | 58.5 | | L | C | C | C | C | L | U | L | L | C | L | C | L | L | C | |
| L | C | L | | C | L | C | C | L | L | U | C | C | C | L | L | C | L | L | |
| L | L | L | | L | L | U | C | L | L | L | L | H | C | L | L | L | U | L | L |
| L | C | U | | C | L | L | L | L | L | L | C | C | L | L | L | L | L | L | L |
| L | L | L | | C | L | C | L | L | C | C | L | C | L | L | U | L | L | L | L |
| C | L | L | | C | C | L | L | U | C | L | | | | | | | | | |
| m323* | 2 | 63.2 | | L | C | C | C | C | L | U | L | L | C | L | C | L | C | C | |
| C | C | L | | L | L | C | C | L | C | L | C | C | L | C | C | C | L | L | C |
| L | L | L | | L | L | U | L | L | L | L | L | C | L | L | L | L | U | C | L |
| L | L | U | | C | L | L | C | L | L | L | L | C | L | L | U | U | L | C | L |
| L | C | L | | C | L | L | L | L | C | L | C | L | C | L | L | C | L | L | C |
| L | L | L | | L | C | L | L | L | C | C | | | | | | | | | |
| m220* | 2 | 64.5 | | L | C | C | C | C | L | U | L | L | C | L | C | L | C | C | |
| L | C | L | | C | L | C | C | L | C | L | C | C | L | C | C | L | L | L | C |
| L | L | L | | L | L | U | L | L | L | L | L | C | C | L | L | L | U | C | L |
| L | L | U | | C | L | L | L | C | L | L | C | C | L | L | C | L | L | C | L |
| L | C | L | | C | L | L | L | L | C | C | L | C | L | L | L | C | L | L | L |
| C | L | L | | L | C | L | L | L | C | C | | | | | | | | | |
| g17288* | 2 | 71 | L | C | C | C | C | L | C | L | L | C | L | C | L | C | C | C | |
| C | L | L | | L | L | C | L | C | L | C | C | L | L | C | C | L | C | L | L |
| L | L | L | | L | L | L | L | L | L | C | L | L | L | L | C | C | L | L | |
| L | C | C | | L | L | L | C | L | L | C | C | L | L | L | L | C | L | L | |
| C | L | C | | L | L | L | L | L | C | L | C | L | C | L | L | C | L | | |
| L | L | L | | C | L | L | L | C | C | | | | | | | | | | |
| g4514* | 2 | 76.4 | | L | C | C | C | C | L | L | L | L | C | L | C | L | C | C | |
| C | C | H | | L | L | L | C | L | L | L | C | U | L | L | C | C | C | L | C |
| L | L | L | | L | L | IL | L | L | L | C | L | L | L | L | IC | L | | | |
| L | L | U | | L | C | C | C | C | C | C | L | L | L | L | C | L | C | L | |
| L | C | L | | C | L | L | L | L | L | L | C | L | C | L | C | L | L | C | |
| L | L | L | | L | C | L | L | L | C | C | | | | | | | | | |
| m336* | 2 | 81.5 | | L | C | U | C | C | L | C | C | L | L | C | C | C | L | C | C |
| C | C | L | | L | L | L | L | L | L | U | C | C | L | L | C | C | C | L | C |
| L | L | L | | C | L | L | L | L | L | C | L | L | L | L | C | C | L | | |
| L | L | C | | C | L | C | C | C | L | C | C | L | L | C | L | C | L | | |
| L | C | C | | C | L | L | L | L | L | L | C | L | C | C | C | L | L | C | |
| L | L | L | | L | L | L | L | C | C | | | | | | | | | | |
| m583* | 3 | 7.7 | | L | C | C | C | L | H | U | C | C | C | L | L | L | C | L | L |
| L | C | C | | C | C | L | C | L | C | L | C | L | C | L | L | L | L | | |
| C | C | L | | C | L | C | L | C | L | L | L | C | L | C | L | U | C | C | L |
| C | C | C | | C | L | C | L | C | C | C | C | L | C | L | C | C | L | | |
| L | C | C | | L | L | L | L | C | C | L | C | L | C | U | L | L | C | L | |
| C | C | L | | C | L | L | C | C | C | | | | | | | | | | |
| g4523* | 3 | 11.8 | | L | C | C | C | L | C | U | C | C | C | L | L | L | C | L | |
| L | L | C | | C | C | C | L | C | L | U | C | L | U | C | L | C | L | L | L |

TABLE 9-continued

| | | | | | | | | | | | | | | | | | | | |
|---|---|---|---|---|---|---|---|---|---|---|---|---|---|---|---|---|---|---|---|
| L | C | L | L | C | L | C | C | C | L | L | C | C | L | C | L | U | C | C | |
| L | C | L | C | C | L | C | L | C | C | C | C | C | L | C | L | C | C | L | |
| C | L | C | C | L | U | C | L | C | C | L | C | L | C | U | L | L | L | C | |
| L | C | C | L | C | L | L | L | C | C | | | | | | | | | | |
| m228* | 3 | 17.5 | | L | C | C | C | U | L | C | C | C | C | L | C | L | C | L | |
| L | L | U | C | C | L | L | C | L | U | C | L | U | C | L | C | L | L | L | |
| L | C | L | L | C | L | L | C | C | L | L | C | C | L | H | L | L | C | C | |
| L | C | L | C | C | C | C | L | L | C | C | C | C | U | U | L | C | L | |
| C | C | C | C | L | C | C | L | C | C | L | C | L | C | U | C | U | L | C | |
| L | C | C | L | C | L | L | U | C | C | | | | | | | | | | |
| g4708* | 3 | 20.9 | | L | C | C | C | L | L | U | C | C | C | L | C | L | C | L | |
| L | L | C | U | C | L | L | C | L | U | C | L | L | C | L | C | L | L | L | |
| L | C | L | L | C | L | L | C | C | L | L | C | C | L | L | L | U | C | C | |
| L | C | L | C | C | C | C | L | L | C | C | C | C | C | C | L | L | C | L | |
| C | C | C | C | L | C | C | L | C | C | L | C | L | C | U | C | L | L | C | |
| L | C | C | L | C | L | L | L | C | C | | | | | | | | | | |
| m105* | 3 | 24.7 | | L | C | C | L | L | L | U | C | C | C | L | C | L | C | L | |
| L | L | C | C | C | L | L | C | L | L | C | L | L | C | L | C | L | L | L | |
| L | C | L | L | C | L | L | C | C | C | L | C | C | C | H | L | U | C | L | |
| L | C | L | C | C | C | C | L | L | C | C | C | C | C | C | L | L | C | L | |
| C | C | C | C | L | C | C | C | C | C | L | C | L | C | C | C | L | L | C | |
| L | L | C | L | C | L | L | L | C | C | | | | | | | | | | |
| g4117* | 3 | 61.5 | | C | L | C | C | L | L | U | C | C | C | L | L | L | C | C | |
| L | C | C | C | C | C | L | C | L | L | C | C | L | C | L | C | L | L | C | |
| L | C | L | L | L | L | L | C | C | C | L | C | C | L | L | L | U | C | L | |
| C | L | L | C | C | C | C | L | L | C | L | C | L | C | L | L | C | C | C | |
| L | L | C | C | C | C | C | C | L | C | C | L | C | L | L | C | L | C | L | |
| C | L | C | L | C | L | L | L | C | C | | | | | | | | | | |
| m249* | 3 | 63.7 | | C | L | C | C | L | L | U | C | C | L | L | L | L | C | C | |
| L | C | C | C | C | C | L | C | L | U | C | C | L | C | L | C | L | L | C | |
| L | C | L | L | L | L | L | C | C | C | C | C | L | L | L | L | U | C | L | |
| C | L | L | C | C | C | C | L | L | C | L | C | L | L | L | L | C | C | C | |
| L | C | L | C | C | C | C | C | L | C | L | C | L | L | C | L | C | L | L | |
| C | L | C | L | C | L | L | L | C | C | | | | | | | | | | |
| g4564b* | 3 | 63.9 | | C | L | C | L | L | L | U | C | C | L | L | L | C | C | |
| L | C | C | C | C | C | C | C | L | U | C | C | U | C | L | C | L | L | C | |
| L | C | L | L | L | L | L | C | C | C | C | L | L | U | L | U | C | L | |
| C | L | L | C | C | C | C | L | C | C | L | C | L | C | U | L | L | C | |
| L | L | C | C | L | C | C | C | L | C | C | U | C | L | U | C | L | C | L | |
| C | L | C | L | C | L | U | U | C | C | | | | | | | | | | |
| m457* | 3 | 71.9 | | C | L | L | L | L | L | U | C | L | C | L | L | L | C | C | |
| C | C | C | L | C | C | C | C | L | C | L | L | C | L | C | L | C | L | C | |
| L | C | L | L | L | L | L | C | C | C | C | L | L | L | L | U | C | C | |
| C | L | L | C | C | C | L | L | C | C | L | C | L | L | C | C | L | L | C | |
| L | L | L | C | C | C | C | C | L | C | C | L | L | C | L | C | L | |
| C | L | C | L | C | L | L | L | C | C | | | | | | | | | | |
| g4014* | 3 | 72 | C | L | U | U | U | L | C | C | L | C | L | L | L | C | C | C | |
| C | C | C | C | C | C | C | L | L | C | C | U | C | L | C | L | C | L | |
| C | L | L | U | L | L | C | C | C | C | L | U | U | L | U | L | C | C | C | |
| L | L | C | C | C | C | L | C | C | L | C | L | L | U | U | L | C | L | |
| L | C | C | L | C | C | C | L | C | C | L | C | L | L | C | L | C | L | C | |
| L | C | L | C | U | L | U | C | C | | | | | | | | | | | |
| g2778* | 3 | 86.3 | | C | L | L | L | C | L | U | C | L | C | L | L | L | C | C | |
| C | C | C | L | L | C | C | C | L | U | C | L | C | L | C | L | C | C | |
| L | C | L | C | L | U | L | C | C | C | C | C | L | L | L | C | U | C | C | |
| C | L | U | C | C | C | L | L | C | C | L | C | C | L | L | U | L | C | C | |
| L | L | L | C | C | C | C | C | L | C | C | U | C | L | U | C | L | C | L | |
| C | L | C | L | C | L | L | L | C | C | | | | | | | | | | |
| m424* | 3 | 91.3 | | C | L | L | C | L | L | U | L | L | C | L | C | L | C | C | |
| C | C | C | L | L | C | C | L | L | U | C | L | L | C | L | L | L | L | C | |
| C | C | L | C | L | U | L | C | C | C | C | C | L | C | L | C | U | C | C | |
| C | L | U | C | C | C | C | L | L | C | C | L | L | C | L | C | L | C | L | |
| L | L | L | C | C | C | C | C | C | C | L | C | L | L | C | L | C | L | |
| C | L | C | L | C | L | L | L | C | C | | | | | | | | | | |
| g3843* | 4 | 4 | | C | L | L | C | C | L | U | C | L | L | L | C | L | C | C | C |
| L | C | L | C | C | C | C | L | U | L | L | C | L | C | L | C | L | C | |
| L | C | L | C | L | C | L | L | L | C | L | L | L | U | C | C | L | |
| L | C | L | C | L | C | L | L | L | C | L | L | L | L | C | C | L | |
| L | C | C | L | L | L | C | C | C | U | L | L | L | L | L | L | L | |
| C | C | L | L | L | C | C | L | L | | | | | | | | | | | |
| g2616* | 4 | 4 | | C | L | L | C | L | L | U | C | L | L | L | C | C | C |
| L | L | L | C | C | C | C | L | L | L | C | L | C | L | L | C | L | |
| L | C | L | C | U | C | C | L | L | C | L | L | L | H | U | C | C | L | |
| L | U | C | L | C | L | C | L | L | C | L | L | L | C | C | C | L | |
| C | C | C | L | L | L | C | C | L | U | L | L | C | L | L | L | L | |
| C | C | L | L | L | C | C | L | L | | | | | | | | | | | |
| m506* | 4 | 14.9 | | C | L | L | C | C | L | U | C | L | L | L | C | C |
| C | L | L | L | C | C | C | C | L | L | L | C | L | C | L | L | C | |
| L | L | C | L | C | U | C | C | L | C | L | L | C | L | L | L | U | C | C |

TABLE 9-continued

| | | | | | | | | | | | | | | | | | |
|---|---|---|---|---|---|---|---|---|---|---|---|---|---|---|---|---|---|
| L | L | U | L | L | C | L | C | C | L | L | L | C | L | L | L | C | C |
| L | L | C | C | L | L | L | L | C | C | L | L | L | L | L | C | L | L |
| L | C | C | L | L | L | C | C | L | L | | | | | | | | |
| m518* | 4 | 30 | C | C | U | C | C | L | U | C | C | C | L | L | L | L | C | L |
| L | C | L | C | C | C | C | L | L | L | L | C | C | C | L | C | L | C | L |
| L | C | L | C | L | C | C | L | C | L | C | C | L | L | L | U | C | C | L |
| L | L | L | L | C | L | C | C | L | L | L | L | C | L | L | L | L | L |
| L | C | C | L | L | L | L | C | C | L | L | L | L | L | C | C | L | L |
| C | C | C | L | C | C | C | L | C | | | | | | | | | |
| pCITd23* | 4 | 31.2 | | C | C | L | C | C | L | C | C | C | C | L | L | L | L | C |
| L | L | C | L | C | C | C | C | L | L | L | L | C | C | C | L | C | L | C |
| L | L | C | L | C | L | C | C | L | C | L | C | C | C | L | L | C | C | C |
| L | L | C | L | L | C | L | C | C | L | L | L | L | L | L | L | L | L |
| L | C | C | C | L | L | L | L | C | C | L | L | L | L | C | C | L | L |
| L | L | C | C | L | C | C | C | L | L | | | | | | | | |
| g6837* | 4 | 39 | C | C | L | C | C | C | C | C | C | L | L | L | L | C | L |
| L | C | U | C | C | C | C | L | L | L | L | C | C | C | C | L | C | L |
| C | C | C | C | L | C | C | L | C | C | C | C | L | C | C | C | C | L |
| C | C | L | L | C | L | L | C | L | L | L | L | L | L | C | L | L | L |
| C | L | C | L | L | L | C | C | L | L | C | L | L | C | C | C | L | H |
| L | C | C | L | C | C | C | C | L | | | | | | | | | |
| m326* | 4 | 39.2 | | C | C | L | C | C | C | C | C | C | C | L | L | L | L | C |
| L | L | C | L | C | C | C | C | L | L | L | L | C | C | C | C | C | C |
| L | C | C | C | C | L | C | C | L | L | C | C | L | L | C | C | C | C |
| L | C | C | L | L | C | L | L | C | L | L | L | L | L | L | C | L | C |
| C | C | L | C | L | L | L | L | C | C | L | L | C | L | L | C | C | L |
| H | L | C | C | L | C | C | C | C | L | | | | | | | | |
| g10086* | 4 | 42.2 | | C | C | L | C | C | U | C | C | C | L | L | L | L | C |
| L | L | C | L | C | C | C | C | L | L | L | L | C | C | C | C | L | C |
| L | C | C | C | C | L | C | C | L | C | C | C | C | L | C | C | C | C |
| L | C | C | L | L | C | U | L | C | L | L | U | L | L | L | L | C | L | C |
| C | C | L | C | L | L | L | L | C | C | L | L | C | L | L | C | C | C | L |
| H | L | C | L | C | C | C | C | L | | | | | | | | | |
| m226* | 4 | 43.7 | | C | C | L | C | C | C | C | C | U | C | L | L | C | L | C |
| L | L | L | L | C | C | C | C | L | L | L | L | C | C | C | C | C | C |
| L | C | C | C | C | L | C | C | C | L | C | C | C | C | L | C | C | L |
| L | C | C | L | L | C | L | L | C | L | L | L | L | L | L | L | C | L | H |
| C | C | L | C | L | L | L | L | C | L | L | L | C | L | L | C | C | C | L |
| U | L | C | C | L | C | C | C | C | C | | | | | | | | |
| g4564a* | 4 | 44 | C | C | L | C | C | C | U | C | C | C | L | L | L | L | C | L |
| L | C | L | C | C | C | L | L | L | L | L | C | C | C | C | L | C | L |
| C | C | C | C | C | L | C | C | C | C | C | L | C | C | C | C | L |
| C | C | L | L | C | L | L | C | L | L | L | L | L | C | L | C | C | C |
| C | L | C | L | L | L | L | C | C | L | C | L | L | C | C | C | L | H |
| L | C | C | L | C | C | C | C | L | | | | | | | | | |
| g3845* | 4 | 51 | C | C | L | C | C | C | C | C | C | L | L | L | L | C | L |
| L | L | U | C | C | C | C | L | L | L | L | U | C | C | C | C | C | L |
| C | C | C | C | L | C | C | C | L | C | C | C | C | L | C | C | C | L | L |
| C | C | L | L | L | C | L | L | C | L | L | L | L | L | C | L | H | C |
| C | L | C | L | L | L | C | L | L | U | C | L | U | C | C | C | L | C |
| L | C | C | L | C | C | C | C | C | | | | | | | | | |
| m600* | 4 | 63.5 | | C | C | C | C | U | L | U | C | C | L | L | L | C | C | C |
| L | L | U | L | C | L | L | C | L | U | C | L | U | C | C | C | U | L | C |
| L | C | C | C | L | U | C | C | C | C | L | C | C | L | C | C | L | L |
| L | C | C | L | C | L | L | C | L | L | L | L | U | U | C | L | H |
| C | C | L | C | L | C | L | L | C | L | L | C | L | U | C | U | C | L |
| C | L | C | C | C | C | C | U | C | L | | | | | | | | |
| g8300* | 4 | 63.9 | | C | C | C | C | C | L | U | C | L | L | L | C | C | C |
| L | L | L | C | C | U | L | C | L | U | C | L | C | C | C | C | L | C |
| L | C | C | C | L | U | C | C | C | L | C | L | C | C | C | C | U | L | L |
| L | C | U | C | L | L | L | C | C | L | L | L | L | C | C | C | L | C |
| C | C | L | C | C | L | C | L | L | L | C | L | U | C | C | C | C | L |
| C | L | C | C | C | L | C | C | C | L | | | | | | | | |
| pCITd99* | 4 | 68 | L | C | C | C | U | L | L | C | C | L | L | L | C | C | C | L |
| L | L | L | C | U | L | C | L | U | C | L | U | C | C | C | L | C | C | L |
| C | C | L | L | U | C | L | C | L | C | L | C | C | C | C | L | L | L |
| C | L | L | U | L | L | L | C | C | L | L | L | U | U | C | L | U | C |
| C | L | C | L | C | L | L | L | L | L | C | L | U | C | U | C | L | C |
| L | C | C | C | L | C | U | C | L | | | | | | | | | |
| g3088* | 4 | 70.4 | | C | C | C | C | L | C | L | U | C | L | L | L | C | L | C |
| L | L | L | U | C | U | L | C | L | U | C | L | C | C | C | L | L | C |
| L | C | C | L | L | L | C | L | C | L | C | L | C | C | C | C | U | L | L |
| L | C | L | L | H | L | L | L | C | L | L | L | C | C | C | L | C | C |
| C | C | C | C | C | C | L | L | L | L | U | C | L | U | C | C | C | L |
| C | L | C | C | C | L | C | C | L | | | | | | | | | |
| g3713* | 4 | 85.4 | | L | C | L | C | C | C | U | C | C | L | L | L | C | C | L |
| L | L | L | L | L | C | L | C | C | U | L | L | C | C | C | L | C | L |
| L | C | L | C | L | C | L | C | L | C | C | L | C | C | C | U | L | L |
| C | C | L | L | C | L | L | L | L | C | L | L | L | L | C | C | L | L | C |

TABLE 9-continued

```
        C    C    L    L    L    C    L    L    L    C    L    U    C    L    C    C    C    L
        C    L    C    C    C    L    C    C    L    L
g3715*  5    8.4       C    C    L    C    L    L    U    L    L    C    L    C    C    L    L    C
        L    L         L    C    L    L    C    L    C    L    L    C    L    L    L    L
        L    L    L    L    C    C    L    L    L    L    L    L    C    L    U    L    L    C
        L    C    L    C    C    L    L    L    L    L    L    C    L    L    C    C    C    L    L
        C    L    L    C    L    L    C    C    L    L    U    C    L    C    C    C    L    L
        C    L    C    L    C    L    C    L    L
m217*   5    10.6      C    C    L    L    L    L    U    L    L    C    L    C    C    L    L
        C    C    L    L    C    L    L    C    L    C    L    L    C    L    C    L    L    L    L
        L    L    L    L    L    C    L    L    L    L    L    L    C    C    U    L    L
        C    C    C    L    L    C    L    L    L    L    L    C    L    C    C    C    L    L
        L    C    L    L    C    L    L    C    C    L    L    C    L    C    C    C    C    L
        L    C    L    C    L    C    L    C    C    L
g3837*  5    14.5      C    C    L    L    L    L    U    L    L    C    L    C    C    L    L
        C    C    L    L    C    C    L    C    L    L    C    L    C    L    L    L    L
        L    L    L    L    L    C    C    L    L    L    L    L    L    C    C    U    L    L
        C    L    C    L    L    C    L    L    L    L    L    C    L    C    C    C    L    L
        L    C    L    L    C    L    L    C    C    L    L    U    C    L    C    C    C    C    L
        L    C    L    C    L    C    L    C    C    L
g4560*  5    27.9      C    C    L    C    L    L    U    L    L    L    L    C    C    C    L
        C    C    C    L    C    C    L    C    L    C    L    L    C    L    L    L    L    L    L
        L    L    L    L    L    U    L    L    C    L    L    L    L    C    C    C    C    U    L    L
        L    L    U    L    L    C    L    L    U    L    L    L    L    C    C    C    L    C
        L    L    L    L    L    L    L    C    C    L    L    C    C    C    L    C    L    C    U
        U    L    L    C    L    C    C    C    C    L
m291*   5    34.4      C    L    C    L    L    C    C    L    L    L    L    C    C    C    L
        C    C    C    L    C    C    L    C    L    C    L    L    L    L    L    L    L    L    L
        L    L    L    L    U    L    L    L    C    L    L    L    C    C    C    C    L    L
        L    L    L    L    C    C    L    L    L    L    L    L    C    C    C    C    L    C
        L    L    L    L    U    U    U    L    L    L    C    C    L    U    L    U    L
        L    L    L    U    U    U    C    C    C    L
m247*   5    52.5      C    C    C    C    C    L    L    U    L    C    L    L    C    C    C    L
        C    L    C    L    C    C    C    C    L    L    L    L    L    L    C    C    L    C
        L    C    C    L    C    C    L    C    C    L    L    C    L    C    L    U    C    L
        C    C    C    C    C    C    L    L    C    L    C    L    C    C    C    L    L
        L    L    L    L    L    L    L    C    L    L    L    L    C    C    C    L    C    C    C
        L    L    C    L    L    C    L    C    C    C
g4028*  5    57.7      L    C    C    C    L    L    U    C    L    L    C    C    C    L
        C    L    C    L    L    C    C    L    L    L    L    L    L    C    C    C    L    C
        L    C    C    L    L    C    L    C    C    L    L    C    L    C    L    U    C    L
        L    C    C    C    C    C    L    C    C    C    L    C    C    L    C    L    L
        C    L    L    L    L    C    L    C    L    L    C    C    C    L    C    L    C    C    C
        L    L    H    L    L    C    L    C    C    C
m435*   5    80.1      L    C    L    L    C    L    U    C    L    C    L    L    C    L    L
        L    L    C    L    L    C    L    C    L    C    L    L    C    L    C    U    C    L
        L    C    C    C    C    L    C    L    C    C    L    C    L    C    L    C    L    C
        C    C    L    L    C    C    C    L    L    C    C    L    C    L    C    C
        L    C    C    L    L    C    C    C    C
g2368*  5    93.5      L    L    L    L    C    L    U    C    L    C    L    L    L    L    L
        L    C    C    L    C    L    C    L    L    C    L    L    C    C    L    L    C
        C    C    C    L    L    C    L    C    L    C    L    C    L    C    L    U    C    L
        C    C    L    C    L    C    L    C    L    L    C    L    C    C    U    C    L
        C    C    C    L    C    C    L    C    L    U    C    C    C    C    C    C    C
        C    C    C    L    C    C    C    C    C
m555*   5    100       L    U    L    L    U    L    C    C    C    L    L    L    L    C
        C    C    L    L    C    L    C    L    U    C    L    L    C    L    L    C    C
        C    C    L    L    C    C    C    C    L    C    L    C    L    C    C    C
        C    C    C    C    C    L    C    L    L    C    C    U    L    C    L    C    C
        C    L    L    C    C    C    L    C    L    L    C    C    C    C    C
        C    L    L    C    C    C    L    C    C
```

TABLE 10

| SOURCE | SUM-OF-SQUARES | DF | MEAN-SQUARE | F-RATIO | P |
|---|---|---|---|---|---|
| \multicolumn{6}{c}{Myrosinase QTL: G29 = m 105 at III:25} ||||||
| \multicolumn{6}{c}{DEP VAR: MYR N: 39 MULTIPLE R: 0.484} ||||||
| \multicolumn{6}{c}{SQUARED MULTIPLE r: 0235} ||||||
| G29 | 4.639 | 1 | 4.639 | 11.344 | 0.002 |
| ERROR | 15.131 | 37 | 0.409 | | |

TABLE 10-continued

| SOURCE | SUM-OF-SQUARES | DF | MEAN-SQUARE | F-RATIO | P |
|---|---|---|---|---|---|
| \multicolumn{6}{c}{Glucosinolate QTL: g19 = g6842 at II:59; g 41 = pCITd23 at IV:31} ||||||
| \multicolumn{6}{c}{DEP VAR: GS N: 38 MULTIPLE R: 0.614} ||||||
| \multicolumn{6}{c}{SQUARED MULTIPLE R: 0.377} ||||||
| G19 | 1.269 | 1 | 1.269 | 9.060 | 0.005 |
| G41 | 1.158 | 1 | 1.158 | 8.270 | 0.007 |

TABLE 10-continued

| SOURCE | SUM-OF-SQUARES | DF | MEAN-SQUARE | F-RATIO | P |
|---|---|---|---|---|---|
| G19*G41 | 0.054 | 1 | 0.054 | 0.383 | 0.540 |
| ERROR | 4.762 | 34 | 0.140 | | |

These results show that marker-assisted selection can be used to identify plant lines having reduced cotyledon or leaf feeding by insect pests of Brassicaceae.

Example 5

Selection for altered glucosinolate levels and myrosinase activity in *Brassica napus*

About 10,000 seeds of *Brassica napus* cultivar IMC-01 (IMC Cargill Foods, Wayzata, Minn.) are preimbibed in 300-seed lots for two hours on wet filter paper to soften the seed coat. The preimbibed seeds are mutagenized by incubating in 80 mM ethyl methanesulfonate (EMS) for four hours. Following mutagenesis, the seeds are rinsed three times in distilled water. The seeds are sown in 48-well flats containing Pro-Mix. About 68 percent of the mutagenized seed will germinate. The plants are maintained at 25°/15°C, 14/10 hour day/night conditions in a greenhouse. At flowering, each plant is individually self-pollinated.

Seed (termed $M_2$ seed) from individual plants is individually catalogued and stored. Approximately 5,000 $M_2$ lines are planted in a summer nursery. The seed from each selfed plant is planted in 3 meter rows with 6 inch row spacing. IMC-01 is planted as the check variety.

Ten cotyledons from $M_2$ seedling rows and IMC-01 control seedling rows are each analyzed in bulk for total non-seed glucosinolate levels as described in Example 1 and for myrosinase activity as described in Example 3. Statistical thresholds for glucosinolate levels and myrosinase activity are established from the control IMC-01 cotyledon analyses. Zar, J., supra, pp. 83–86. Those plants exceeding the statistical thresholds for both increased total non-seed glucosinolates and increased myrosinase activity are self-pollinated by bagging the main raceme of each plant. At maturity, selfed plants are individually harvested and $M_4$ seeds are catalogued and stored.

$M_4$ seed is planted in a greenhouse in 4 inch pots containing Pro-Mix soil and the plants maintained at 25°/15° C, 14/10 hour day/night cycle. Cotyledons from $M_4$ seedlings and IMC-01 controls are individually analyzed for glucosinolate levels and myrosinase activity as described above. Statistical thresholds are established from 250 IMC-01 control seedlings. At flowering, the terminal raceme is self-pollinated by bagging. At maturity, $M_5$ seed from plants exceeding the statistical threshold for glucosinolate and myrosinase is individually harvested from each $M_4$ plant, labeled and stored.

Selected $M_5$ seed is planted in a field trial in 3 meter rows with 6 inch row spacing. Cotyledons from 10 $M_5$ seedlings in each row are analyzed for glucosinolate and myrosinase as described above, using the same Z-distribution as for $M_4$ population. Plants exceeding the statistical threshold are self-pollinated and the remaining open-pollinated plants in the same row are bulk harvested.

Selected $M_6$ seed is entered into field trials at 4 locations in eastern Idaho. The four locations are chosen to have differences among the locations in growing conditions. The selected $M_6$ seed lines are planted in four 3-meter rows with an 8-inch spacing. Each plot is replicated four times. The planting design is a randomized complete block. The cultivars IMC-01, Westar, Global and Cyclone are used as check cultivars. Cotyledons of 10 seedlings from each block are analyzed for glucosinolate and myrosinase levels as described above. Cotyledon and leaf damage by flea beetles and lepidopteran larvae are estimated as describe in Example 1. $M_6$ plants are also evaluated for agronomic characteristics such as yield, standability, disease resistance and seed characteristics such as low erucic acid and low seed glucosinolate levels. The plots are harvested at maturity and the yield of each entry is determined by taking the statistical average of the four replications.

The Least Significant Difference test is used to rank the entries for yield, insect damage, total non-seed glucosinolate levels and myrosinase activity. $M_6$ lines show statistically significant increases in total non-seed glucosinolate levels and myrosinase activity, compared to check varieties. $M_6$ lines also show statistically significant reductions in susceptibility to insect damage compared to check varieties. Those $M_6$ lines inheriting increased non-seed glucosinolate and myrosinase activities as well as other desired characteristics, are advanced to subsequent field trials.

To the extent not already indicated, it will be understood by those of ordinary skill in the art that any one of the various specific embodiments herein described and illustrated may be further modified to incorporate features shown in other of the specific embodiments.

The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. A method for producing a cruciferous plant having a heritable reduction in susceptibility to cotyledon or leaf feeding by Phyllotreta insects, comprising the steps of:
   a) selecting, in a population of $P_0$ Brassicaceae plants having a mean total non-seed glucosinolate level, at least one $P_0$ plant having a total non-seed glucosinolate level that is decreased sufficiently, relative to said total non-seed glucosinolate level in said $P_0$ population, to reduce susceptibility to cotyledon or leaf feeding by Phyllotreta insects;
   b) producing $P_1$ progeny from said at least one $P_0$ plant;
   c) identifying at least one $P_1$ plant that inherits said decreased total glucosinolate level, thereby producing said plant having said reduced susceptibility to cotyledon or leaf feeding by said insects.

2. The method of claim 1, wherein said $P_1$ progeny are produced by selfing.

3. The method of claim 1, wherein said selecting step comprises selecting a plurality of $P_0$ plants having a total non-seed glucosinolate level that is decreased sufficiently, relative to said total non-seed glucosinolate level in said $P_0$ population, to reduce cotyledon or leaf feeding by Phyllotreta insects and wherein said $P_1$ progeny are produced by crosses among said plurality of $P_0$ plants.

4. The method of claim 1, wherein said $P_0$ population comprises plants grown from mutagenized seeds.

5. The method of claim 1, wherein said at least one $P_0$ plant or said at least one $P_1$ plant is identified by genetic linkage between said decreased total non-seed glucosinolate level and a polymorphic genetic marker.

6. The method of claim 5, wherein said genetic marker comprises a nucleic acid having substantial sequence similarity to about 50 nucleotides from Arabidopsis RFLP probe g6842.

7. The method of claim 5, wherein said genetic marker comprises a nucleic acid having substantial sequence similarity to about 50 nucleotides from Arabidopsis RFLP probe pCITd23.

8. The method of claim 1, wherein said $P_0$ plant is selected from plants in the 0–15 percentile for total non-seed glucosinolates in said $P_0$ population.

9. The method of claim 1, wherein said plant is a *Brassica campestris* plant.

10. The method of claim 1, wherein said plant is a *Brassica napus* plant.

11. The method of claim 1, wherein said Phyllotreta insects comprise Phyllotreta cruciferae.

12. A method for producing a cruciferous plant having a heritable reduction in cotyledon or leaf feeding by Phyllotreta insects, comprising the steps of:

a) selecting, in a population of $P_0$ Brassicaceae plants having a mean myrosinase activity, at least one $P_0$ plant having a level of myrosinase activity that is increased sufficiently, relative to said myrosinase activity in said $P_0$ population, to reduce susceptibility to cotyledon or leaf feeding by cruciferous insects;

b) producing $P_1$ progeny from said at least one $P_0$ plant;

c) identifying at least one $P_1$ plant that inherits said increased myrosinase activity, thereby producing said plant having said reduced susceptibility to cotyledon or leaf feeding by said insects.

13. The method of claim 12, wherein said $P_1$ progeny are produced by selfing.

14. The method of claim 12, wherein said selecting step comprises selecting a plurality of $P_0$ plants having a myrosinase level that is increased sufficiently, relative to said myrosinase activity in said $P_0$ population, to reduce susceptibility to cotyledon or leaf feeding by Phyllotreta insects and wherein said $P_1$ progeny are produced by crosses among said plurality of $P_0$ plants.

15. The method of claim 12, wherein said $P_0$ population comprises plants grown from mutagenized seeds.

16. The method of claim 12, wherein said $P_0$ plant is identified by genetic linkage between said increased myrosinase activity and a polymorphic genetic marker.

17. The method of claim 16, wherein said genetic marker comprises a nucleic acid having substantial sequence similarity to about 50 nucleotides from Arabidopsis RFLP probe m105.

18. The method of claim 12, wherein said $P_0$ plant is selected from plants in the 85–100 percentile for myrosinase activity in said $P_0$ population.

19. The method of claim 12, wherein said plant is a *Brassica campestris* plant.

20. The method of claim 12, wherein said plant is a *Brassica napus* plant.

21. The method of claim 12, wherein said Phyllotreta insects comprise Phyllotreta cruciferae.

22. The method of claim 12, wherein said at least one $P_0$ plant is further selected to have a level of total non-seed glucosinolates that is increased sufficiently, relative to a mean total non-seed glucosinolate level in said $P_0$ population, to reduce susceptibility to cotyledon or leaf feeding by cruciferous insects.

23. A cruciferous plant produced by the method of claim 1.

24. A cruciferous plant produced by the method of claim 12.

25. A cruciferous plant produced by the method of claim 22.

* * * * *